United States Patent [19]
Townsend et al.

[11] Patent Number: 5,248,672
[45] Date of Patent: Sep. 28, 1993

[54] POLYSUBSTITUTED BENZIMIDAZOLE NUCLEOSIDES AS ANTIVIRAL AGENTS

[75] Inventors: Leroy B. Townsend; John C. Drach, both of Ann Arbor, Mich.

[73] Assignee: The Regents of the University of Michigan, Ann Arbor, Mich.

[21] Appl. No.: 607,899

[22] Filed: Nov. 1, 1990

[51] Int. Cl.$^5$ .................. A61K 31/70; C07H 19/23
[52] U.S. Cl. .................... 514/43; 536/28.9
[58] Field of Search .................. 536/24, 28.9; 514/43

[56] References Cited

U.S. PATENT DOCUMENTS

| | | | |
|---|---|---|---|
| 2,935,508 | 5/1960 | Shunk et al. | 536/23 |
| 3,037,980 | 6/1962 | Hitchings et al. | 536/24 |
| 3,311,628 | 3/1967 | Partyka | 544/280 |
| 3,631,036 | 12/1971 | Kim et al. | 536/24 |
| 3,817,982 | 6/1974 | Verheyden et al. | 536/24 |
| 3,867,386 | 2/1975 | Kim et al. | 544/280 |
| 3,962,211 | 6/1976 | Townsend et al. | 536/24 |
| 4,199,574 | 4/1980 | Schaeffer | 424/200 |
| 4,229,453 | 10/1980 | Roth et al. | 424/251 |
| 4,596,798 | 6/1986 | Shipman, Jr. et al. | 514/183 |
| 4,892,865 | 1/1990 | Townsend et al. | 514/43 |
| 4,927,830 | 5/1990 | Townsend et al. | 514/258 |
| 4,968,686 | 11/1990 | Townsend et al. | 514/258 |

FOREIGN PATENT DOCUMENTS

| | | |
|---|---|---|
| 3036390 | 5/1982 | Fed. Rep. of Germany. |
| 3145287 | 5/1983 | Fed. Rep. of Germany. |
| 03142 | 5/1988 | World Int. Prop. O.. |

OTHER PUBLICATIONS

Tamm, I., "Inhibitor of Influenza and Mumps Virus Multiplication by 4,5,6,-(or 5,6,7,-) Trichloro-1--D-Ribofuranosyl-benzimidazole," Science, 120:847-848 (1954).

Townsend, L. B. et al., "Benzimidazole Nucleosides, Nucleotides, and Related Derivatives," Chemical Reviews, 70:389-438 (1970).

Zou, R., "Synthesis and Antiviral Activity of 1--D-Ribofuranosyl-2,4,6-Tri-Chlorobenzimidazole," American Chemical Society, Apr. 1990.

Devivar, R. V. et al., "The Formation of an Unusual Product During Studies on the Diazotization of Certain 2-Aminobenzimidazoles," American Chemical Society, Apr. 1990.

Hayflick, L. "Screening Tissue Cultures for Mycoplasma Infections," in P. F. Kruse, Jr. and M. K. Patterson, Jr. (ed), Tissue culture:methods and applications Academic Press Inc., New York, 1973, pp. 722-728.

Drach et al., "Comparison of Activity of Tubercidin Analogs Against Herpesviruses," 28th ICAAC, Los Angeles, Calif., Oct. 1988.

Saluja, S. et al., "Synthesis and Antiviral Activity of Certain 2-Substituted 4,5,6,7-Tetrachlorobenzimidazole Acyclic Nucleosides," American Chemical Society, Apr. 1990.

Nassiri et al., "Kinetic Assessment by Flow Cytometry of the Effect of Two New Antiviral Drugs on the Cell Cycle," 3rd Annual Meeting Clinical Application of Cytometry, Sep. 1988.

Duffy, T., et al., "Pyrrolo[2,3-d] pyrimidines, Synthesis from 4-Pyrimidyhydrazones, a 2-Bis(methylthio)methyleneaminopyrrolo-3-carbonitrile, and a Pyrrolo[2-,3-d][1,3]thiazine-2(1H)-thione", J. Chem. Soc., 16:1921-1929 (1974).

Sigma Chemical Co. Catalog, St. Louis, Mo., 1984, p. 898.

(List continued on next page.)

Primary Examiner—Johnnie R. Brown
Assistant Examiner—Gary L. Kunz
Attorney, Agent, or Firm—Harness, Dickey & Pierce

[57] ABSTRACT

This invention relates to novel polysubstituted benzimidazole nucleosides and compositions and their use in the treatment of viral infections, particulary those caused by human cytomegalovirus and herpes simplex virus. Such substituted compounds exhibit antiviral properties superior to their parent compounds and low levels of cytotoxicity.

24 Claims, 7 Drawing Sheets

OTHER PUBLICATIONS

Saxena, N. K., et al., "Synthesis and Antiviral Activity of Certain 4-Substituted and 2,4-Disubstituted 7-[(-2-Hydroxyethoxy)methyl]pyrrolo[2,3-d]pyrimidines", *J. Med. Chem.*, 31:1501–1506 (1988).

Robins, M. J., et al., "Nucleic acid related compounds.24.Transformation of tubercidin 2',3'-O-orthoscetape into halo, deoxy, epoxide, and unsaturated sugar nucleosides[1,2]" 55:1251–1259 (1977).

Drach, J. C., et al., "Tritiated Thymidine Incorporation Does Not Measure DNA Synthesis in Ribavirin-Treated Human Cells", *Science*, 212:549–551 (1981).

Shipman, C., Jr., et al., "Evaluation of 4-(2-Hydroxyethyl)-1-piperazineethanesulfonic Acid (HEPES) as a Tissue Culture Buffer", *Proc. Soc. Exp. Biol. Med.* 120:305–310 (1969).

Gupta, P. K., et al., "Synthesis, Cytotoxicity, and Antiviral Activity of Some Acyclic Analogues of the Pyrrolo[2,3-d]pyrimidine Nucleoside Antibiotics Tubercidin, Toyocamycin, and Sangivamycin" *J. Med. Chem.*, 32:402–408 (1989).

Puolo, J. S., et al., "Synthesis and Antiviral Activity of Certain 4-and 4,5-Disubstituted 7-[(2-Hydroxyethoxy)methyl]pyrrolo[2,3-d]pyrimidines", *J. Med. Chem.*, 31:2086–2092 (1988).

Vindelov, L. L., "Flow Mirofluorometric Analysis of Nuclear DNA in Cells from Solid Tumors and Cell Suspensions" *Virchow's Arch. Cell Pathol.* 24:227–242 (1977).

Gadler, H., "Nucleic Acid Hybridization for Measurement of Effects of Antiviral Compounds on Human Cytomegalovirus DNA Replication", *Antimicrob. Agents Chemother.*, 24:370–374 (1983).

Ramasamy, K., et al., "Total Synthesis of 2'-Deoxytoyocamycin, 2'-Deoxysangivamycin and Related 7-β-D-Arabinofuranosyl-Pyrrolo[2,3-d]Pyrimidines via Ring Closure of Pyrrole Precursors Prepared by the Stereospecific Sodium Salt Glycosylation Procedure", Nucleic Acid Research Institute, (Abstract 65).

Tolman, R. L., et al., "Pyrrolopyrimidine Nucleosides III The Total Synthesis of Toyocamycin, Sangivamycin, Tubercidin, and Related Derivatives", *J. Am. Chem. Soc.* 91:2102–2108 (1969).

Robins, M. J., et al., "A Mild Conversion of Vicinal Diols to Alkenes, Efficient Transformation of Ribonucleosides into 2'-ene and 2',3'-Dideoxynucleosides", *Tetrahedron Letters*, 25:367–370 (1984).

Jain, T. C. et al., "Reactions of 2-Acyloxyisobutyryl Halides with Nucleosides. III. Reactions of Tubercidin and Formycin", *J. Org. Chem.*, 38:3179–3186 (1973).

DeClercq, E., et al., "Nucleic Acid Related Compounds. 51. Synthesis and Biological Properties of Sugar-Modified Analogues of the Nucleoside Antibiotics Tubercidin, Toyocamycin, Sangivamycin, and Formycin", *J. Med. Chem.* 30:481–486 (1987).

Hansske, F., et al., "2' and 3'-Ketonucleosides and their Arabino and Xylo Reduction Products", *Tetrahedron* 40:125–135 (1984).

Smith, C. M., et al. "Inhibitors of Hypoxanthine Metabolism in Ehrlich Ascites Tumor Cells in Virto", *Cancer Treatment Reports*, 60:1567–1584 (1976).

Maruyama, T., et al., "Pyrrolopyrimidine Nucleosides. 18. Synthesis and Chemotherapeutic Acitivity of 4-Amino-7-(3-deoxy-β-D-ribofuranosyl)pyrrolo-[2,3-d]pyrimidine-5-carboxamide (3'-Deoxysangivamycin) and 4-Amino-7-(2-deoxy-β-D-ribofuranosyl)-pyrrolo[2,3-d]pyrimidine-5-carboxamide (2'-Deoxysangivamycin)" *J. Med. Chem.*, 26:25–29 (1983).

Mitsuya, H., et al. "3'-Azido-3'-deoxythymidine (BW A5090): An Antiviral agent that inhibits the infectivity and cytopathic effect of human T-lymphotropic virus type III/lymphadenopathy-associated virus in vitro", *PNAS (USA)*, 82:7096–7100 (1985).

Mitsuya, H., et al., "Inhibition of the in vitro infectivity and cytopathic effect of human T-lymphotrophic virus type III/lymphadenopathy-associated virus (HTLV-III/LAV) by 2',3'-dideoxynucleosides", *PNAS (USA)*, 83:1911–1915 (1986).

DeClercq, E., et al., "Antirhinovirus Activity of Purine Nucleoside Analogs", *Antimicrob. Agents Chemother.*, 29:482–484 (1986).

Shipman, C., Jr., "Antiviral Activity of Arabinosyladenine and Arabinosylhypoxanthine in Herpes Simplex Virus-Infected KB Cells; Selective Inhibition of Viral Deoxyribonucleic Acid Synthesis in Synchronized Suspension Cultures", *Antimicrob. Agents Chemother.*, 9:120–127 (1976).

Bergstom, D., et al., "Antiviral Activity of C-5 Substituted Tubercidin Analogues" *J. Med. Chem.*, 27:285–292 (1984).

Turk, S. R., et al., "Pyrrolo[2,3-d]Pyrimidine Nucleosides as Inhibitors of Human Cytomegalovirus", *Antimicrob. Agents Chemother.*, 31:544–550 (1987).

| Compound # | R  | $R_1$ | $R_2$  | $R_3$  | $R_4$ | $R_5$ |
|------------|----|-------|--------|--------|-------|-------|
| 45         | H  | H     | Cl     | Cl     | H     | Cl    |
| 52         | H  | H     | Cl     | Cl     | H     | Br    |
| 60         | Ac | H     | $NO_2$ | $NO_2$ | H     | Cl    |
| 61         | H  | H     | $NO_2$ | $NO_2$ | H     | Cl    |
| 80         | Ac | Cl    | H      | Cl     | H     | Cl    |
| 81         | H  | Cl    | H      | Cl     | H     | Cl    |
| 83a        | H  | H     | Cl     | Cl     | H     | I     |
| 84         | Ac | Br    | Br     | H      | H     | Cl    |
| 85         | H  | Br    | Br     | H      | H     | Cl    |
| 95         | H  | H     | Br     | Cl     | H     | Cl    |
| 99         | H  | H     | Cl     | Br     | H     | Cl    |
| 107        | H  | H     | I      | I      | H     | Cl    |

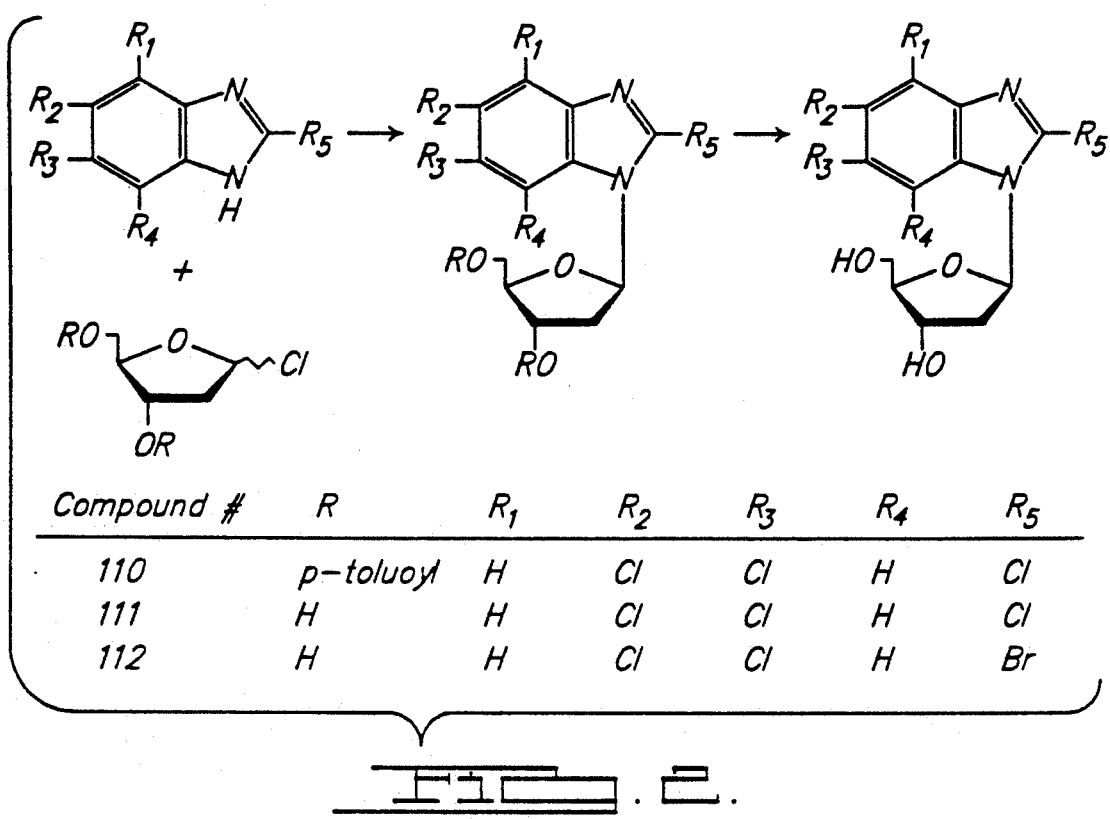

FIG. 2.

Effect Of Compound 45 on The Replication Of Herpes Viruses

| | | 50% Inhibitory Concentration, $\mu M$ | |
|---|---|---|---|
| VIRUS | CELL LINE | VIRUS | CYTOTOXICITY [a] |
| HSV-1 | Human Foreskin Fibroblasts | >57 | ~140 |
| HSV-1 | Rabbit Kidney | >284 | >284 |
| HSV-1 | Mouse Embryo Fibroblasts | 28 | ~140 |
| HSV-2 | Human Foreskin Fibroblasts | >57 | ~140 |
| HSV-2 | Rabbit Kidney | >284 | >284 |
| HSV-2 | Mouse Embryo Fibroblasts | 14 | ~140 |
| VZV | Human Foreskin Fibroblasts | 94 | --- |
| MCMV | Mouse Embryo Fibroblasts | 57 | ~140 |
| HCMV | Human Foreskin Fibroblasts | 1.4 | >>28 |

[a] Visual cytotoxicity in cell line used to propogate virus.

FIG. 4.

Antiviral Activity And Cytotoxcity

| Compound Number[a] | 50% Inhibitory Concentration | | | | | |
|---|---|---|---|---|---|---|
| | Antiviral Activity Against: | | | Cytotoxicity In Cell Line: | | |
| | HCMV | | HSV-1 | | | |
| | Plaque | Yield[b] | Plaque | HFF[c] | BSC[c] | KB[d] |
| 45 | 2.8 | 1.4 | 151 | 242 | >100 | 129 |
| 52 | 0.2 | 0.3 | 99 | 100 | | >100 |
| 61 | 2 | 37 | 27 | 32 | | 10 |
| 81 | 10.8 | | >100 | 32 | | >100 |
| 83a | 15 | 35 | 21 | >100 | | 23 |
| 85 | 3.8 | 1.2 | 55 | 50 | | >100 |
| 95 | 6.5 | 1.8 | >100 | 100 | | >100 |
| 99 | 10.4 | 3.3 | >100 | 100 | | >100 |
| 107 | 0.9 | 50 | 50 | 10 | | 19 |
| 111 | 20 | 12 | 41 | >320 | | >100 |
| DRB[e] | 42 | 19 | 30 | 24 | | 39 |

[a] Number for chemical structure presented in text.

[b] 90% inhibitory concentration ($I_{90}$) presented.

[c] Visual cytotoxcity scored on HFF or BSC-1 cells at time of HCMV or HSV-1 plaque enumeration.

[d] Average percent inhibition of DNA, RNA and protein systhesis or cell growth determined in KB cells as described in the text.

[e] Initially described by I. Tamm; Science 120:847-848, 1954.

FIG. 3.

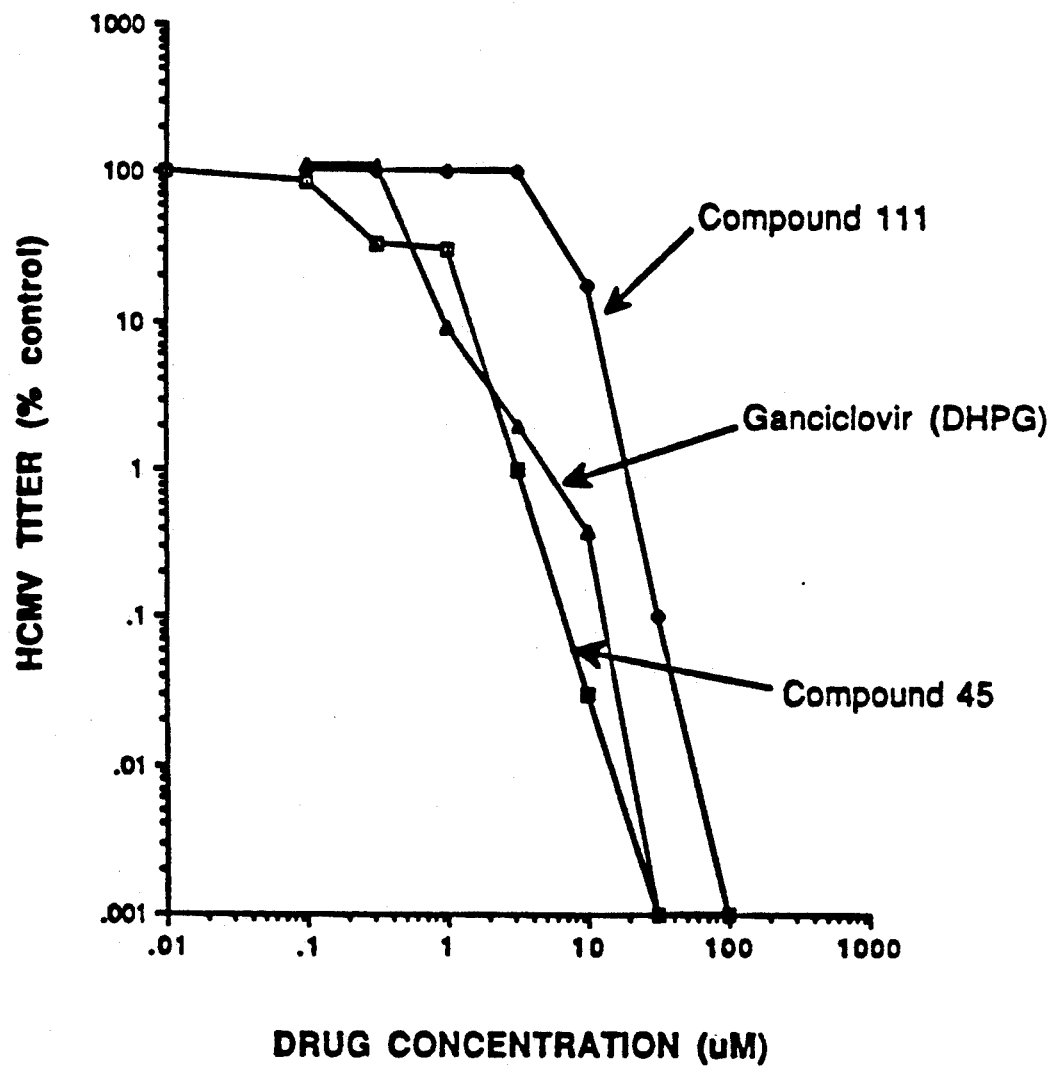
Figure 5. HCMV Titer Reduction by Benzimidazole Nucleosides and Ganciclovir

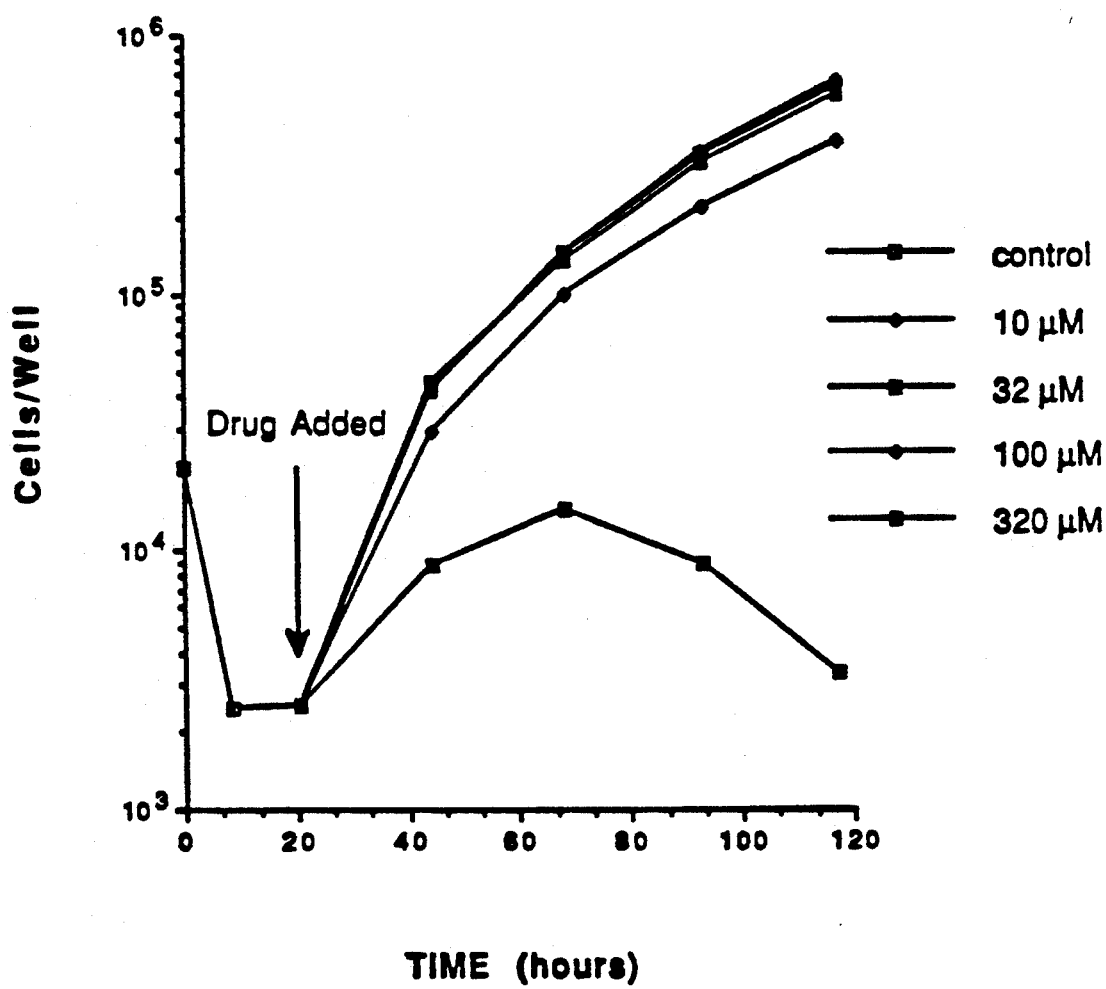
Figure 6. KB Cell Growth in the Presence of Compound 45

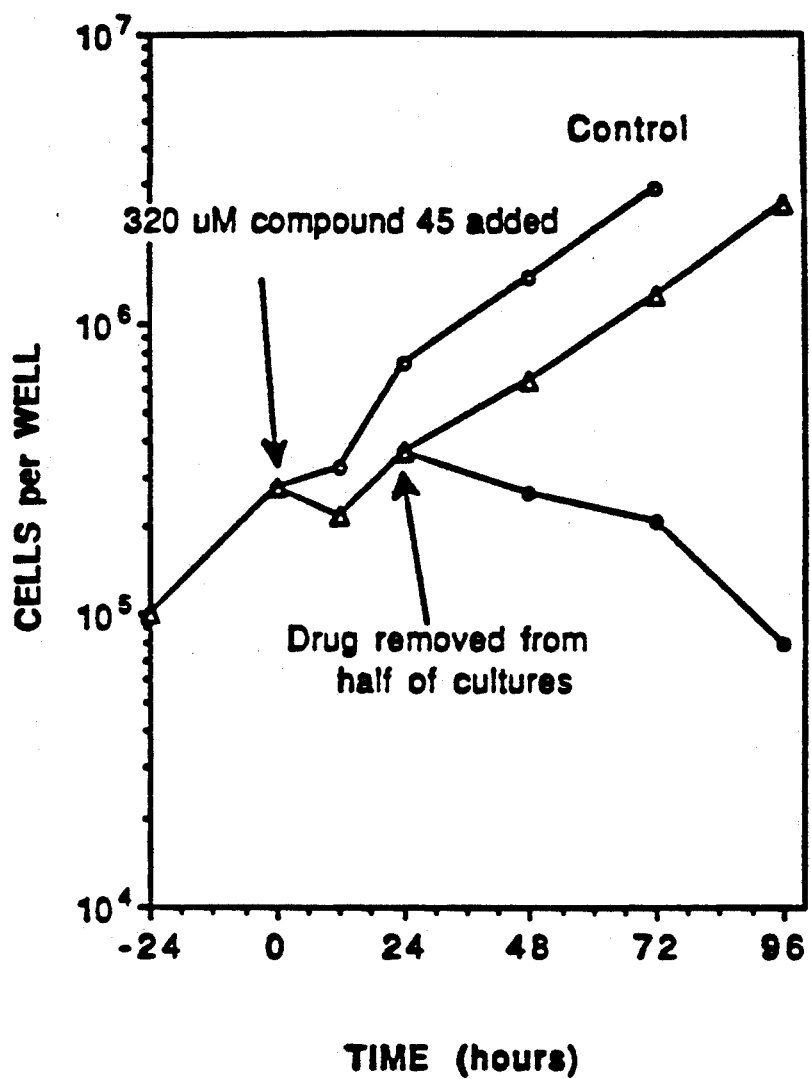
Figure 7. Reversibility of the Effect of Compound 45 on the Growth of KB Cells

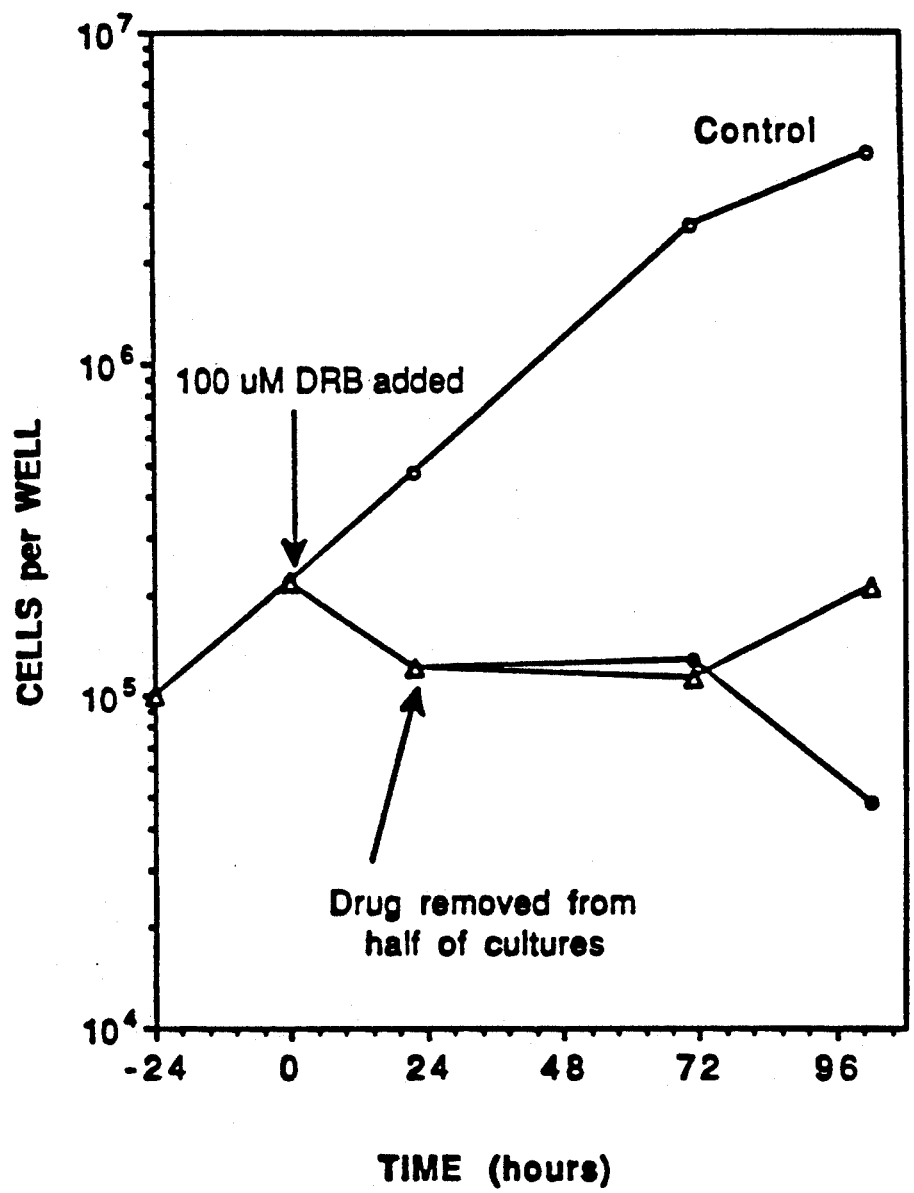
Figure 8. Effect of DRB on the Growth of KB CELLS

POLYSUBSTITUTED BENZIMIDAZOLE NUCLEOSIDES AS ANTIVIRAL AGENTS

SPONSORSHIP

This invention was made with government support under Contract No. NO1 Al 42554 and NO1 Al 72641 awarded by the National Institute of Allergy and Infectious Diseases of the National Institutes of Health. The government has certain rights in this invention.

FIELD OF THE INVENTION

The present invention relates generally to polysubstituted benzimidazole nucleosides and, more particularly, to novel polysubstituted benzimidazole nucleosides and compositions and their use as antiviral agents against viruses such as human cytomegalovirus and herpes simplex virus.

BACKGROUND OF THE INVENTION

Antiviral activity of the bicyclic nucleosides such as 5,6-dichloro-1-($\beta$-D-ribofuranosyl) benzimidazole (DRB) and some closely related derivatives has been previously reported. Activity of those compounds against specific viruses, such as the RNA viruses, has also been reported.

Benzimidazole nucleosides are particularly attractive as potential antiviral agents because of their stability toward some major pathways of bioactive purine (bicyclic) nucleoside inactivation, e.g., deamination by adenosine deaminase and glycosidic bond cleavage by purine nucleoside phosphorylases. Unfortunately, benzimidazole nucleosides such as DRB which have been previously described as having antiviral activity also have generally unacceptable levels of cytotoxicity, thereby greatly diminishing their usefulness in the treatment of viral infections in animals. It would thus be very desirable to develop derivatives of these compounds having increased antiviral properties with decreased cytotoxicity.

SUMMARY OF THE INVENTION

The present invention relates to novel compositions comprising a polysubstituted benzimidazole nucleoside and a pharmaceutically acceptable carrier, wherein the polysubstituted benzimidazole nucleoside is selected from the group consisting of compounds having the following formulas and pharmaceutically acceptable salts and formulations thereof:

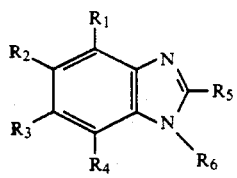

where $R_1$ is H, $R_2$ is Cl, $R_3$ is Cl, $R_4$ is H, $R_5$ is Br and $R_6$ is $\beta$-D-ribofuranosyl;

$R_1$ is H, $R_2$ is Cl, $R_3$ is Cl, $R_4$ is H, $R_5$ is Br and $R_6$ is 2'-deoxy-$\beta$-D-ribofuranosyl;

$R_1$ is H, $R_2$ is Cl, $R_3$ is Cl, $R_4$ is H, $R_5$ is I and $R_6$ is $\beta$-D-ribofuranosyl;

$R_1$ is H, $R_2$ is Cl, $R_3$ is Cl, $R_4$ is H, $R_5$ is Cl and $R_6$ is 2'-deoxy-$\beta$-D-ribofuranosyl;

$R_1$ is H, $R_2$ is Br, $R_3$ is Cl, $R_4$ is H, $R_5$ is Cl and $R_6$ is $\beta$-D-ribofuranosyl;

$R_1$ is H, $R_2$ is Cl, $R_3$ is Br, $R_4$ is H, $R_5$ is Cl and $R_6$ is $\beta$-D-ribofuranosyl;

$R_1$ is H, $R_2$ is I, $R_3$ is I, $R_4$ is H, $R_5$ is Cl and $R_6$ is $\beta$-D-ribofuranosyl;

$R_1$ is H, $R_2$ is NO$_2$, $R_3$ is NO$_2$, $R_4$ is H, $R_5$ is Cl and $R_6$ is $\beta$-D-ribofuranosyl;

$R_1$ is Br, $R_2$ is Br, $R_3$ and $R_4$ are H, $R_5$ is Cl and $R_6$ is $\beta$-D-ribofuranosyl;

$R_1$ is Cl, $R_2$ is H, $R_3$ is Cl, $R_4$ is H, $R_5$ is Cl and $R_6$ is $\beta$-D-ribofuranosyl; and $R_1$ is H, $R_2$ is Cl, $R_3$ is Cl, $R_4$ is H, $R_5$ is Cl and $R_6$ is $\beta$-D-ribofuranosyl.

As used herein, "pharmaceutically acceptable carrier" means any composition, solvent, dispersion medium, coating, delivery vehicle and the like, which can be employed to administer the compounds and compositions of the present invention without undue physiological effects.

The present invention also relates to the method of treatment of viral infections with a therapeutically effective amount of an aforementioned polysubstituted benzimidazole nucleoside and pharmaceutically acceptable salts and formulations thereof. By "therapeutically effective amount" is meant an amount effective to achieve a selected desired result in the treatment of a viral infection in accordance with the present invention.

The present invention further relates to a novel polysubstituted benzimidazole nucleoside, wherein the polysubstituted benzimidazole nucleoside is selected from the group consisting of compounds having the following formulas and pharmaceutically acceptable salts and formulations thereof:

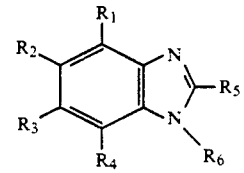

where $R_1$ is H, $R_2$ is Cl, $R_3$ is Cl, $R_4$ is H, $R_5$ is Br and $R_6$ is $\beta$-D-ribofuranosyl;

$R_1$ is H, $R_2$ is Cl,. $R_3$ is Cl, $R_4$ is H, $R_5$ is Br and $R_6$ is 2'-deoxy-$\beta$-D-ribofuranosyl;

$R_1$ is H, $R_2$ is Cl, $R_3$ is Cl, $R_4$ is H, $R_5$ is I and $R_6$ is $\beta$-D-ribofuranosyl;

$R_1$ is H, $R_2$ is Cl, $R_3$ is Cl, $R_4$ is H, $R_5$ is Cl and $R_6$ is 2'-deoxy-$\beta$-D-ribofuranosyl;

$R_1$ is H, $R_2$ is Br, $R_3$ is Cl, $R_4$ is H, $R_5$ is Cl and $R_6$ is $\beta$-D-ribofuranosyl;

$R_1$ is H, $R_2$ is Cl, $R_3$ is Br, $R_4$ is H, $R_5$ is Cl and $R_6$ is $\beta$-D-ribofuranosyl;

$R_1$ is H, $R_2$ is I, $R_3$ is I, $R_4$ is H, $R_5$ is Cl and $R_6$ is $\beta$-D-ribofuranosyl;

$R_1$ is H, $R_2$ is NO$_2$, $R_3$ are NO$_2$, $R_4$ is H, $R_5$ is Cl and $R_6$ is $\beta$-D-ribofuranosyl; and $R_1$ is Br, $R_2$ is Br, $R_3$ is H, $R_4$ is H, $R_5$ is Cl and $R_6$ is $\beta$-D-ribofuranosyl.

BRIEF DESCRIPTION OF THE DRAWINGS

FIGS. 1 and 2 are synthesis schemes and tables of polysubstituted benzimidazoles in accordance with the principles of the present invention.

FIG. 3 is a table of antiviral activity and cytotoxicity of polysubstituted benzimidazoles in accordance with the principles of the present invention.

FIG. 4 is a table of the effects of a polysubstituted benzimidazole nucleoside on the replication of selected herpes viruses in accordance with the principles of the present invention.

FIG. 5 is a dose response curve comparing the activity against human cytomegalovirus of two polysubstituted benzimidazole nucleosides to the known drug ganciclovir in accordance with the principles of the present invention.

FIG. 6 is a graph illustrating the low degree of cytotoxicity (cell growth inhibition) of a polysubstituted benzimidazole nucleoside in accordance with the principles of the present invention.

FIG. 7 is a graph illustrating the reversibility of the cytotoxic effects produced by a very high level of a polysubstituted benzimidazole nucleoside in accordance with the principles of the present invention.

FIG. 8 is a graph illustrating the cytotoxic effects of DRB on cell growth and its irreversibility.

DETAILED DESCRIPTION OF THE PREFERRED EMBODIMENTS OF THE INVENTION

A. Chemical Structure of Compounds

Figure 1:
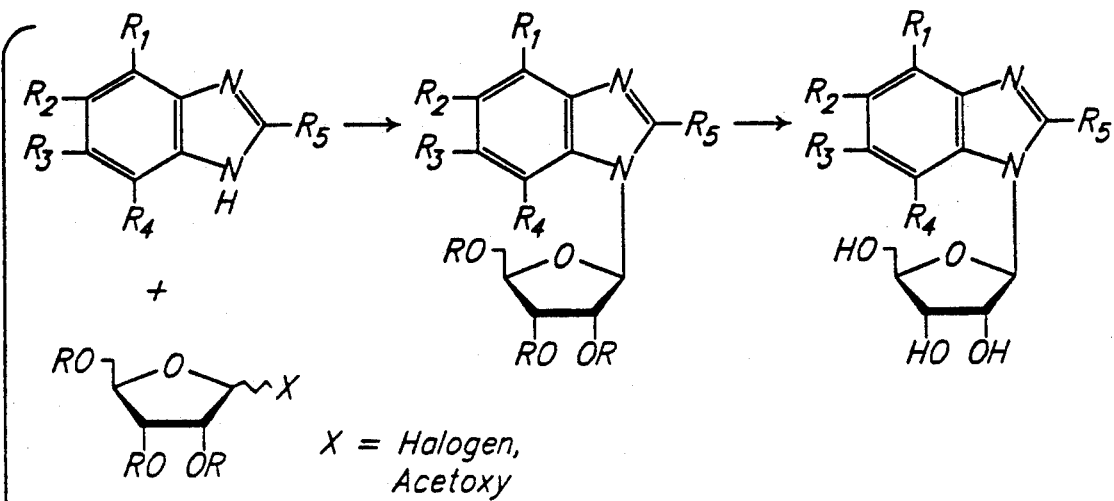

The present invention relates to novel compositions comprising a polysubstituted benzimidazole nucleoside and a pharmaceutically acceptable carrier, wherein the polysubstituted benzimidazole nucleoside is selected from the group consisting of compounds having the following formulas and pharmaceutically acceptable salts and formulations thereof:

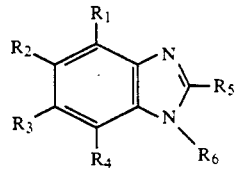

where
$R_1$ is H, $R_2$ is Cl, $R_3$ is Cl, $R_4$ is H, $R_5$ is Br and $R_6$ is $\beta$-D-ribofuranosyl;
$R_1$ is H, $R_2$ is Cl, $R_3$ is Cl, $R_4$ is H, $R_5$ is Br and $R_6$ is 2'-deoxy-$\beta$-D-ribofuranosyl;
$R_1$ is H, $R_2$ is Cl, $R_3$ is Cl, $R_4$ is H, $R_5$ is I and $R_6$ is $\beta$-D-ribofuranosyl;
$R_1$ is H, $R_2$ is Cl, $R_3$ is Cl, $R_4$ is H, $R_5$ is Cl and $R_6$ is 2'-deoxy-$\beta$-D-ribofuranosyl;
$R_1$ is H, $R_2$ is Br, $R_3$ is Cl, $R_4$ is H, $R_5$ is Cl and $R_6$ is $\beta$-D-ribofuranosyl;
$R_1$ is H, $R_2$ is Cl, $R_3$ is Br, $R_4$ is H, $R_5$ is Cl and $R_6$ is $\beta$-D-ribofuranosyl;
$R_1$ is H, $R_2$ is I, $R_3$ is I, $R_4$ is H, $R_5$ is Cl and $R_6$ is $\beta$-D-ribofuranosyl;
$R_1$ is H, $R_2$ is NO$_2$, $R_3$ is NO$_2$, $R_4$ is H, $R_5$ is Cl and $R_6$ is $\beta$-D-ribofuranosyl;
$R_1$ is Br, $R_2$ is Br, $R_3$ and $R_4$ are H, $R_5$ is Cl and $R_6$ is $\beta$-D-ribofuranosyl;
$R_1$ is Cl, $R_2$ is H, $R_3$ is Cl, $R_4$ is H, $R_5$ is Cl and $R_6$ is $\beta$-D-ribofuranosyl; and
$R_1$ is H, $R_2$ is Cl, $R_3$ is Cl, $R_4$ is H, $R_5$ is Cl and $R_6$ is $\beta$-D-ribofuranosyl.

The present invention further relates to the treatment of viral infections by contacting the infected host with a therapeutically effective amount of a polysubstituted benzimidazole nucleoside selected from the group consisting of compounds having the following formulas and pharmaceutically acceptable salts and formulations thereof:

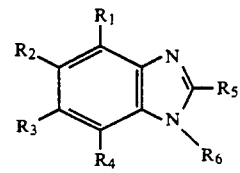

where
$R_1$ is H, $R_2$ is Cl, $R_3$ is Cl, $R_4$ is H, $R_5$ is Br and $R_6$ is $\beta$-D-ribofuranosyl;
$R_1$ is H, $R_2$ is Cl, $R_3$ Cl, $R_4$ is H, $R_5$ is Br and $R_6$ is 2'-deoxy-$\beta$-D-ribofuranosyl;
$R_1$ is H, $R_2$ is Cl, $R_3$ is Cl, $R_4$ is H, $R_5$ is I and $R_6$ is $\beta$-D-ribofuranosyl;
$R_1$ is H, $R_2$ is Cl, $R_3$ is Cl, $R_4$ is H, $R_5$ is Cl and $R_6$ is 2'-deoxy-$\beta$-D-ribofuranosyl;
$R_1$ is H, $R_2$ is Br, $R_3$ is Cl, $R_4$ is H, $R_5$ is Cl and $R_6$ is $\beta$-D-ribofuranosyl;
$R_1$ is H, $R_2$ is Cl, $R_3$ is Br, $R_4$ is H, $R_5$ is Cl and $R_6$ is $\beta$-D-ribofuranosyl;
$R_1$ is H, $R_2$ is I, $R_3$ is I, $R_4$ is H, $R_5$ is Cl and $R_6$ is $\beta$-D-ribofuranosyl;
$R_1$ is H, $R_2$ is NO$_2$, $R_3$ is NO$_2$, $R_4$ is H, $R_5$ is Cl and $R_6$ is $\beta$-D-ribofuranosyl;
$R_1$ is Br, $R_2$ is Br, $R_3$ is H, $R_4$ is H, $R_5$ is Cl and $R_6$ is $\beta$-D-ribofuranosyl;
$R_1$ is Cl, $R_2$ is H, $R_3$ is Cl, $R_4$ is H, $R_5$ is Cl and $R_6$ is $\beta$-D-ribofuranosyl; and
$R_1$ is H, $R_2$ is Cl, $R_3$ is Cl, $R_4$ is H, $R_5$ is Cl and $R_6$ is $\beta$-D-ribofuranosyl.

The present invention further relates to a novel polysubstituted benzimidazole nucleoside selected from the group consisting of compounds having the following formulas and pharmaceutically acceptable salts thereof:

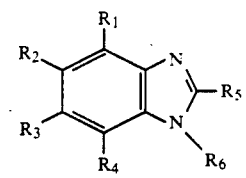

where
$R_1$ is H, $R_2$ is Cl, $R_3$ is Cl, $R_4$ is H, $R_5$ is Br and $R_6$ is $\beta$-D-ribofuranosyl;
$R_1$ is H, $R_2$ is Cl, $R_3$ is Cl, $R_4$ is H, $R_5$ is Br and $R_6$ is 2'-deoxy-$\beta$-D-ribofuranosyl;
$R_1$ is H, $R_2$ is Cl, $R_3$ is Cl, $R_4$ is H, $R_5$ is I and $R_6$ is $\beta$-D-ribofuranosyl;
$R_1$ is H, $R_2$ is Cl, $R_3$ is Cl, $R_4$ is H, $R_5$ is Cl and $R_6$ is 2'-deoxy-$\beta$-D-ribofuranosyl;
$R_1$ is H, $R_2$ is Br, $R_3$ is Cl, $R_4$ is H, $R_5$ is Cl and $R_6$ is $\beta$-D-ribofuranosyl;
$R_1$ is H, $R_2$ is Cl, $R_3$ is Br, $R_4$ is H, $R_5$ is Cl and $R_6$ is $\beta$-D-ribofuranosyl;
$R_1$ is H, $R_2$ is I, $R_3$ is I, $R_4$ is H, $R_5$ is Cl and $R_6$ is $\beta$-D-ribofuranosyl;

$R_1$ is H, $R_2$ is $NO_2$, $R_3$ is $NO_2$, $R_4$ is H, $R_5$ is Cl and $R_6$ is β-D-ribofuranosyl; and $R_1$ is Br, $R_2$ is Br, $R_3$ is H, $R_4$ is H, $R_5$ is Cl and $R_6$ is β-D-ribofuranosyl;

Compounds in the practice of the present invention include:

(1) 2,5,6-trichloro-1-(2'-deoxy-β-D-ribofuranosyl)-benzimidazole where $R_1,R_4$=H; $R_2,R_3,R_5$=Cl; $R_6$=2'-deoxy-β-D-ribofuranosyl (denoted compound 111 in text);

(2) 5,6-dichloro-2-bromo-1-(β-D-ribofuranosyl)benzimidazole where $R_1,R_4$=H; $R_2,R_3$=Cl; $R_5$=Br; $R_6$=β-D-ribofuranosyl (denoted compound 52 in text);

(3) 5,6-dichloro-2-iodo-1-(β-D-ribofuranosyl)benzimidazole where $R_1,R_4$=H; $R_2,R_3$=Cl; $R_5$=I; $R_6$=β-D-ribofuranosyl (denoted compound 83a in text);

(4) 2-chloro-5,6-dinitro-1-(β-D-ribofuranosyl)benzimidazole where $R_1,R_4$=H; $R_2,R_3$=$NO_2$; $R_5$=Cl; $R_6$=β-D-ribofuranosyl (denoted compound 61 in text);

(5) 2,4,6-trichloro-1-(β-D-ribofuranosyl)benzimidazole where $R_2,R_4$=H; $R_1$, $R_3$, $R_5$=Cl; $R_6$=β-D-ribofuranosyl (denoted compound 81 in text);

(6) 2-chloro-5,6-diiodo-1-(β-D-ribofuranosyl)benzimidazole where $R_1$, $R_4$=H; $R_2,R_3$=I; $R_5$=Cl; $R_6$=β-D-ribofuranosyl (denoted compound 107 in text);

(7) 5-bromo-2,6-dichloro-1-(β-D-ribofuranosyl)benzimidazole where $R_1,R_4$=H; $R_2$=Br; $R_3,R_5$=Cl; $R_6$=β-D-ribofuranosyl (denoted compound 95 in text);

(8) 6-bromo-2,5-dichloro-1-(β-D-ribofuranosyl)benzimidazole where $R_1,R_4$=H; $R_3$=Br; $R_2,R_5$=Cl; $R_6$=β-D-ribofuranosyl (denoted compound 99 in text);

(9) 2-chloro-4,5-dibromo-1-(β-D-ribofuranosyl)benzimidazole where $R_3$, $R_4$=H; $R_1$, $R_2$=Br; $R_5$=Cl; $R_6$=β-D-ribofuranosyl (denoted compound 85 in text);

(10) 2,5,6-trichloro-1-(β-D-ribofuranosyl)benzimidazole where $R_1$, $R_4$=H; $R_2$, $R_3$, $R_5$=Cl and $R_6$=β-D-ribofuranosyl (denoted compound 45 in text).

(11) 5,6-dichloro-2-bromo-1-(2'-deoxy-β-D-ribofuranosyl)benzimidazole where $R_1$, $R_4$=H; $R_2$, $R_3$=Cl; $R_5$=Br; $R_6$=2'-deoxy-β-D-ribofuranosyl (denoted compound 112 in text).

Preferred novel compounds of the present invention include:

(1) 2,5,6-trichloro-1-(2'-deoxy-β-D-ribofuranosyl)-benzimidazole where $R_1$, $R_4$=H; $R_2$, $R_3$, $R_5$=Cl; $R_6$=2'-deoxy-β-D-ribofuranosyl (denoted compound 111 in text);

(2) 5,6-dichloro-2-bromo-1-(β-D-ribofuranosyl)benzimidazole where $R_1,R_4$=H; $R_2$, $R_3$=Cl; $R_5$=Br; $R_6$=β-D-ribofuranosyl (denoted compound 52 in text).

(3) 2-chloro-4,5-dibromo-1-(β-D-ribofuranosyl)benzimidazole where $R_3,R_4$=H; $R_1,R_2$=Br; $R_5$=Cl; $R_6$=β-D-ribofuranosyl (denoted compound 85 in text).

Preferred compositions and compounds used in the methods of the present invention include:

(1) 2,5,6-trichloro-1-(2'-deoxy-β-D-ribofuranosyl)-benzimidazole where $R_1$, $R_4$=H; $R_2$, $R_3$, $R_5$=Cl; $R_6$=2'-deoxy-β-D-ribofuranosyl (denoted compound 111 in text);

(2) 5,6-dichloro-2-bromo-1-(β-D-ribofuranosyl)benzimidazole nucleoside where $R_1,R_4$=H; $R_2$, $R_3$=Cl; $R_5$=Br; $R_6$=β-D-ribofuranosyl (denoted compound 52 in text);

(3) 2,5,6-trichloro-1-(β-D-ribofuranosyl)benzimidazole where $R_1$, $R_4$=H; $R_2$, $R_3$, $R_5$=Cl; $R_6$=β-D-ribofuranosyl (denoted compound 45 in text);

(4) 2-chloro-4,5-dibromo-1-(β-D-ribofuranosyl)benzimidazole where $R_3,R_4$=H; $R_1,R_2$=Br; $R_5$=Cl; $R_6$=β-D-ribofuranosyl (denoted compound 85 in text).

B. methods of Use of Compounds

The compounds used in the practice of the present invention exhibit antiviral activity and acceptable cytotoxicity. In particular, it has been found that these compounds are very effective against viruses of the herpes family. The compounds are thus useful in the treatment of viral infections in vivo caused by human cytomegalovirus (HCMV) and herpes simplex viruses types 1 and 2. Other viruses contemplated to be treated within the scope of the present invention include, but are not limited to: varicella-zoster virus (varicella; zoster, chickenpox; shingles); Epstein-Barr virus (infectious mononucleosis; glandular fever; and Burkit's lymphoma); human immunodeficiency virus and hepatitis viruses.

The compounds of the present invention can be used in the treatment of viral infections in animals in accordance with conventional procedures, such as an active ingredient in pharmaceutical compositions, and can be provided as pharmaceutically acceptable salts including, e.g., thiolate, citrate and acetate salts. The pharmaceutical compositions can be administered topically, orally, or parentally and may take the form of tablets, lozenges, granules, capsules, pills, ampoules or suppositories. They may also take the form of ointments, gels, pastes, creams, sprays, lotions, suspensions, solutions and emulsions of the active ingredient in aqueous or nonaqueous diluents, syrups, granulates or powders. In addition to a compound of the present invention, the pharmaceutical compositions can also contain other pharmaceutically active compounds or a plurality of compounds of the invention.

It will be appreciated that appropriate dosages of the compounds and compositions of the invention may depend on the type and severity of the viral infection and may vary from patient to patient. Determining the optimal dosage will generally involve the balancing of the level of therapeutic benefit against any risk or deleterious side effects of the antiviral treatments of the present invention.

C. Methods of Synthesis

The compounds of the present invention can be synthesized in accordance with the representative procedures described vide infra.

The appropriate benzimidazole analog was prepared and then condensed with the appropriate precursor for the ultimate $R_6$ group as represented by Tables 1 and 2 of FIGS. 1 and 2. This has furnished substituted benzimidazole nucleosides and nucleoside analogs which have potential antiviral activity, per se, and are also amenable toward subsequent chemical transformations to afford additional compounds. The solvents, reagents and reaction conditions for the preparation of some representative starting materials, intermediate and target compounds are presented in detail as follows:

Examples of Specific Chemical Synthesis

The compound numbering in this section refers to reaction scheme and table numbers of the compounds.

2,5,6-Trichlorobenzimidazole

Method A

A solution of 5,6-dichlorobenzimidazole-2-one (5 g, 2.5 mmole) in 75 ml of $POCl_3$ was heated at reflux for 5 hours. HCl gas was passed into the mixture for the last ½ hour. Excess $POCl_3$ was removed in vacuo and the residue was decomposed with HCl (150 ml). The brown solid was removed by filtration and washed with $H_2O$ (100 ml). The filtrate was made slowly basic with $NH_4OH$. After cooling, the precipitate was filtered, the precipitate was dissolved in MeOH and an insoluble material was removed by filtration. The filtrate was evaporated under diminished pressure to dryness. The residue was applied to a column of silica gel (Kiesel Gel 70-230 mesh) and eluted with $CH_2Cl_2$. The fractions containing the product were combined, and evaporated to dryness. Yield 1.36 g (25.0%).

Method B

A $CuCl_2$ saturated aqueous solution (15 ml) was diluted to 25 ml with water. Sodium nitrite (1.035 g, 5 mmole) was dissolved in 5 ml of water and slowly added to the $CuCl_2$ solution. After two minutes, 2-amino-5,6-dichlorobenzimidazole (0.935 g, 5 mmole) was slowly added in small portions. The mixture was stirred at room temperature for 1 hr. Excess $CuCl_2$ solution was added and the mixture was heated on a steam bath for 1 hr. The aqueous solution was then extracted with ethyl acetate (3×50 ml) and the organic layer was washed with brine, dried with $MgSO_4$, concentrated, and separated on a silica column using 2% $MeOH/CHCl_3$ to afford 545 mg (49.5%) of 2,5,6-trichlorobenzimidazole. $^1H$ NMR, TLC, and MS analysis were identical to the same compound obtained by Method A.

2-Bromo-5,6-dichlorobenzimidazole

2-Amino-5,6-dichlorobenzimidazole (3 g, 16 mmole) was suspended in 150 ml of water and brought into solution with 2 ml of HBr. Sodium nitrite (3.3 g, 55 mmole) was then added and the mixture was stirred at room temperature for 1 hr. Excess $CuBr_2$ was then added and the mixture was heated on a steam bath for 1 hr. The aqueous solution was extracted with ethyl acetate (3×100 ml), dried with $MgSO_4$, concentrated, and crystallized from ethyl ether to give 1.13 g (26%) of 2-bromo-5,6-dichlorobenzimidazole. $^1H$ NMR (DMSO-$d_6$) δ7.81 ppm (s, 2H), 13.62 (s, 1H). GC/MS: m/e 266, 185, 158, 150, 133, 124, 107, 97, 88, 73, 62, 52, 37.

2,5,6-Trichloro-1-(β-D-ribofuranosyl)benzimidazole (45)

2,5,6-Trichlorobenzimidazole (700 mg, 0.0032 moles) was dissolved in acetonitrile and BSTFA (1 ml, 0.0038 moles) was added. The mixture was heated at 75° C. for 20 minutes. TMSTf (1 ml, 0.0051 moles) and 1-O-acetyl-2,3,5-tri-O-benzoyl-β-D-ribofuranose (1.9 g, 0.0038 moles) were added while heating was continued for 45 min. The acetonitrile was removed under reduced pressure and the protected nucleoside was separated on a silica column, eluting with chloroform. The benzoyl protecting groups were removed by overnight treatment at room temperature with methanolic ammonia. The nucleoside was separated on a column using 50% EtOAc/hexane and then 10% $MeOH/CHCl_3$. The isolated compound was recrystallized from methanol. Yield: (74%); MP: 185°-186° C.; TLC (10% $MeOH/CHCl_3$): Rf=0.20; $^1H$ NMR (DMSO-$d_6$) δ3.68 ppm (q, 2H), 4.00 (d, 1H), 4.12 (t, 1H), 4.40 (q, 1H), 5.28 (d, 1H), 5.41 (t, 1H), 5.49 (d, 1H), 5.57 (d, 1H), 7.96 (s, 1H), 8.55 (s, 1H); $^{13}C$ NMR (DMSO-$d_6$, Broad band decoupling): d 61.08 ppm, 69.80, 71.70, 86.47, 89.16, 114.93, 120.04, 125.77, 125.97, 132.30, 140.96, 142.16; MS (Fast Atom Bombardment): m/e (M+6) 359, (M+4) 357, (M+2) 355, (M+) 353, 319, 285, 263, 221, 187, 177, 133, 115, 103, 97, 85.

2-Bromo-5,6-dichloro-1-(β-D-ribofuranosyl)benzimidazole (52)

2-Bromo-5,6-dichlorobenzimidazole (1 g, 3.8 mmole) was dissolved in dry acetonitrile (150 ml) and stirred in an inert atmosphere at 60° C. BSA (1.03 ml, 4.2 mmole) was added and the mixture was stirred for 10 minutes. 1,2,3,5-Tetra-O-acetyl-β-D-ribofuranose (1.21 g, 3.8 mmole) and TMSTf (0.81 ml, 4.2 mmole) were added to the clear solution and the mixture was stirred for 10 minutes. An additional quantity of 1,2,3,5-tetra-O-acetyl-D-ribofuranose (1.21 g, 3.8 mmole) and TMSTf (0.81 ml, 4.2 mmole) were added to the clear solution and the mixture was allowed to stir at 60° C. for 1 hr. The mixture was concentrated under reduced pressure and separated on a silica column to give the protected 2-bromo-5,6-dichlorobenzimidazole nucleoside. $^{13}C$ NMR ($CDCl_3$): δ170.26 ppm, 169.50, 168.99, 142.97, 132.32, 130.71, 128.09, 128.06, 121.09, 112.98, 88.09, 80.76, 71.01, 69.50, 62.87, 20.97, 20.49, 20.13. $^1H$ NMR ($CDCl_3$): δ2.02 ppm (s, 3H), 2.16 (s, 3H), 2.29 (s, 3H), 4.38 (m, 1H), 4.46 (ddd, 2H), 5.43 (dd, 1H), 5.48 (t, 1H), 6.17 (d, 1H), 7.78 (s, 1H), 7.81 (s, 1H). The protected nucleoside was stirred overnight at room temperature in a methanolic ammonia solution, concentrated, and suspended in methanol (3×25 ml) to yield 2-bromo-5,6-dichloro-1-(β-D-ribofuranosyl)benzimidazole nucleoside in 37%. $^{13}C$ NMR (DMSO-$d_6$): δ142.57 ppm, 132.60, 132.57, 125.76, 119.86, 114.73, 90.21, 86.35, 71.55, 69.76, 61.05. $^1H$ NMR (DMSO-$d_6$): δ3.69 ppm (m, 2H), 3.99 (m, 1H), 4.11 (m, 1H), 4.41 (q, 1H), 5.27 (d, 1H), 5.40 (t, 1H), 5.45 (d, 1H), 5.87 (d, 1H), 7.95 (s, 1H), 8.56 (s, 1H). MS (FAB): m/e 399, 351, 319, 285, 267, 219, 187, 153, 133, 103, 85.

2-Chloro-5,6-dinitro-1-(2,3,5-tri-O-benzyl-β-D-ribofuranosyl)benzimidazole (60)

To a mixture of 0.541 g (2.23 mmol) of 2-chloro-5,6-dinitrobenzimidazole in 12 mL of MeCN, was added 0.558 mL (2.23 mmol) of BSA. The reaction mixture was stirred at 75° C. for 15 min to give a clear solution. This solution was treated with the above MeCN solution of 2,3,5-tri-O-benzyl-D-ribofuranosyl chloride and 0.56 mL (2.90 mmol) of TMSOTf at 75° C. for 30 min. The reaction mixture was cooled and diluted with EtOAc (50 mL). The EtOAc solution was washed with sat. $NaHCO_3$ solution (50 mL×2), sat. NaCl solution (50 mL), dried ($Na_2SO_4$), and evaporated. The residue was chromatographed on a silica column (2.2×18 cm, eluted with 20% EtOAc/hexane). Evaporation of fractions 10-14 (20 mL per fraction) gave 0.502 g (35%) of 60 as a syrup. MS: (FAB) m/e 645 (1%, $MH^+$ =645). $^1H$ NMR (DMSO-$d_6$): δ8.50, 8.49 (2×s, 2, 7-H and 4-H), 7.34, 6.90 (2×m, 15, 3×Ph), 6.09 (d, 1, 1'-H, $J_{1'-2'}=8.0$ Hz), 4.73~4.27 (m, 9, 2'-H, 3'-H, 4'-H, and 3×PhC$\underline{H}_2$), 3.77 (dd, 1, 5'-H, $J_{4'-5'}=2.0$ Hz, $J_{5'-5''}=11.0$ Hz), 3.65 (dd, 1, 5''-H, $J_{4'-5''}=2.5$ Hz).

2-Chloro-5,6-dinitro-1-β-D-ribofuranosylbenzimidazole (61)

To a solution of 0.464 g (0.719 mmol) of 60 in 12 mL of CH$_2$Cl$_2$, was added dropwise 8.4 mL of 1M BCl$_3$ at −78° C. The reaction mixture was stirred at −78° C. for 2 h and then at −40° C. for 2 h. MeOH (5 mL) was added and stirring was continued at −40° C. for 10 min. The reaction mixture was diluted with EtOAc (75 mL). The EtOAc solution was washed with cold H$_2$O (50 mL), sat. NaHCO$_3$ solution (50 mL), sat. NaCl solution (50 mL), dried (Na$_2$SO$_4$), and evaporated. The residue was coevaporated with MeOH (3 x) and then suspended in a small amount of CHCl$_3$ for a few hours. The solid product was filtered to give 0.209 g of 61. This sample was contaminated by a small amount of 2-chloro-5,6-dinitrobenzimidazole. A part of the sample (0.18 g) was purified on a silica column (2.4×10 cm, eluted with pure EtOAc). Evaporation of the appropriate fractions and crystallization by addition of CHCl$_3$ gave 0.084 g of 61 as a white solid. MP: 132°–135° C. MS: (EI) m/e 374.0276 (1%, M+=374.0265). $^1$H NMR (DMSO-d$_6$): δ9.18 (s, 1, 7-H), 8.60 (s, 1, 4-H), 6.00 (d, 1, 1'-H, $J_{1'-2'}=7.5$ Hz), 5.59 (d, 1, 2'-OH, $J_{2'-2'OH}=6.0$ Hz), 5.52 (t, 1, 5'-OH, $J_{5'-5'OH}=4.5$ Hz), 5.38 (d, 1, 3'-OH, $J_{3'-3'OH}=4.5$ Hz), 4.01 (m, 1, 2'-H, $J_{2'-3'}=5.5$ Hz), 4.16 (m, 1, 3'-H, $J_{3'-4'}=2.0$ Hz), 4.07 (m, 1, 4'-H, $J_{4'-5'}=J_{4'-5''}=2.5$ Hz), 3.73 (m, 2, 5'-H and 5''-H, $J_{5'-5''}=12.0$ Hz). $^{13}$C NMR (DMSO-d$_6$): δ146.55 (C2), 142.63 (C3a), 138.90, 138.60 (C5 and C6), 134.12 (C7a), 116.67 (C4), 111.62 (C7), 89.98 (C1'), 86.91 (C4'), 72.86 (C2'), 69.84 (C3'), 60.85 (C5'). Anal. Calcd. for C$_{12}$H$_{11}$ClN$_4$O$_8$: C, 38.47; H, 2.96; N, 14.95. Found: C, 38.46; H, 2.98; N, 14.62.

1-(2,3,5-Tri-O-acetyl-β-D-ribofuranosyl)-2,4,6-trichlorobenzimidazole (80)

To a suspension of 1.362 g (6.15 mmol) of 2,4,6-trichlorobenzimidazole in 31 mL of MeCN, was added 1.52 mL (6.15 mmol) of BSA. The reaction mixture was stirred at 80° C. for 15 min to give a clear solution. This solution was treated with 2.153 g (6.675 mmol) of 1,2,3,5-tetra-O-acetyl-β-D-ribofuranose and 1.426 mL (7.380 mmol) of TMSOTf at 80° C. for 1 h. The reaction mixture was cooled and diluted with EtOAc (150 mL). The EtOAc solution was washed with sat. NaHCO$_3$ solution (150 mL×2), sat. NaCl solution (150 mL), dried (Na$_2$SO$_4$), and evaporated. The residue was coevaporated with MeOH and then suspended in 50 mL of hot MeOH. The suspension was cooled, filtered, and the solid product was washed with MeOH to give 2.103 g of 80 as white crystals (This product showed one spot on TLC). The mother liquor was evaporated and the residue was chromatographed on a silica column (2.5×20 cm, eluted with CHCl$_3$ and 0.5% MeOH/CHCl$_3$). Evaporation of fractions 20–24 (20 mL per fraction) and recrystallization from MeOH gave an additional 0.258 g of 80 as white crystals. The total yield of 80 was 2.361 g (80%). MP: 198°–200° C. MS: (EI) m/e 480.0069 (4%, for C$_{18}$H$_{17}$$^{35}$ClN$_2$$^{37}$ClN$_2$O$_7$: M+=480.0072). $^1$H NMR (DMSO-d$_6$): δ7.89 (d, 1, 7-H, $J_{7-5}=2.0$ Hz), 7.58 (d, 1, 5-H), 6.26 (d, 1, 1'-H, $J_{1'-2'}=7.0$ Hz), 5.54 (t, 1, 2'-H, $J_{2'-3'}=7.0$ Hz), 5.44 (dd, 1, 3'-H, $J_{3'-4'}=4.5$ Hz), 4.48, 4.38 (2×m, 3, 4'-H and 5'-H), 2.14, 2.02 (2×s, 9, 3×Ac). $^{13}$H NMR (DMSO-d$_6$): δ169.84, 169.37, 169.09 (3×COCH$_3$), 140.91 (C2), 137.39 (C3a), 134.14 (C7a), 128.47 (C6), 123.66 (C4), 123.25 (C5), 111.06 (C7), 86.91 (C1'), 79.58 (C4'), 70.54 (C2'), 68.55 (C3'), 62.47 (C5'), 20.48, 20.19, 19.90 (3×COCH$_3$). Anal. Calcd. for C$_{18}$H$_{17}$Cl$_3$N$_2$O$_7$: C, 45.07; H, 3.57; N, 5.84. Found: C, 45.08; H, 3.62; N, 5.87.

2,4,6-Trichloro-1-β-D-ribofuranosylbenzimidazole (81)

A mixture of 0.130 g (0.271 mmol) of 80 in 5 mL of conc. NH$_4$OH/dioxane (1:1 by volume) was stirred in a pressure bottle at room temperature for 1 day. Volatile materials were removed by evaporation and coevaporation with MeOH (3 x, bath temperature <40° C.). The resulting solid was absorbed on silica gel and was chromatographed on a silica column (2×5 cm, eluted successively with 1%, 2%, 3% MeOH/CHCl$_3$). Evaporation of fractions 23–39 (5 mL per fraction) gave a white solid. This solid was washed with H$_2$O, dried to give 46 mg (48%) of 80 as a white solid. MP: 165°–167° C. $^1$H NMR (DMSO-d$_6$): δ8.36 (d, 1, 7-H, $J_{7-5}=2.0$ Hz), 7.52 (d, 1, 5-H), 5.90 (d, 1, 1'-H, $J_{1'-2'}=8.0$ Hz), 5.49 (d, 1, 2'-OH, $J_{2'-2'OH}=6.5$ Hz), 5.38 (t, 1, 5'-OH, $J_{5'-5'OH}=4.5$ Hz), 5.28 (d, 1, 3'-OH, $J_{3'-3'OH}=4.5$ Hz), 4.41 (m, 1, 2'-H, $J_{2'-3'}=5.5$ Hz), 4.14 (m, 1, 3'-H, $J_{3'-4'}=2.0$ Hz), 4.02 (m, 1, 4'-H, $J_{4'-5'}=J_{4'-5''}=2.5$ Hz), 3.70 (m, 2, 5'-H and 5''-H, $J_{5'-5''}=12.0$ Hz). $^{13}$H NMR (DMSO-d$_6$): δ141.64 (C2), 137.50 (C3a), 134.17 (C7a), 128.02 (C6), 123.22 (C4), 122.77 (C5), 112.56 (C7), 89.35 (C1'), 86.52 (C4'), 71.71 (C2'), 69.70 (C3'), 61.02 (C5'). Anal. Calcd. for C$_{12}$H$_{11}$Cl$_3$N$_2$O$_4$: C, 40.76; H, 3.14; N, 7.92. Found: C, 40.74; H, 3.37; N, 7.71.

2-Iodo-5,6-dichloro-1-β-D-ribofuranosylbenzimidazole (83a)

2-Amino-5,6-dichloro-1-(2,3,5-tri-O-acetyl-β-D-ribofuranosyl)benzimidazole nucleoside (43) (50 mg, 0.1 mmole) was added to 3 mL of diiodomethane and amyl nitrite (0.13 ml, 1 mmole) under an inert atmosphere and heated to 50° C. for 1 hour. The mixture was concentrated under reduced pressure and chromatographed on a silica gel column to give one product which was treated with methanolic ammonia for 18 hours. The product was isolated, recrystallized and characterized as compound 83a. $^1$H NMR (DMSO-d$_6$): δ3.71 (m, 2H), 4.07 (m, 1H), 4.12 (m, 1H), 4.40 (q, 1H), 5.23 (m, 1H), 5.37 (m, 2H), 5.82 (d, 1H), 7.89 (s, 1H), 8.52 (s, 1H). $^{13}$C NMR (DMSO-d$_6$): δ145.33 ppm, 132.51, 125.26, 125.18, 119.51, 114.22, 110.32, 92.11, 86.22, 71.47, 69.99, 61.11. MP: 180°–182° C. UV λ$_{max}$ nm (ε×10$^4$): (pH 7) 230 (.490), 259 (.216), 292 (.277), 302 (.305); (pH 1) 230 (.342), 258 (.095), 294 (.301), 303 (.313); (pH 11) 228 (.560), 258 (.198), 292 (.249), 302 (.267). Anal. Calcd. for C$_{12}$H$_{11}$Cl$_2$IN$_2$O$_4$ 1.5CH$_3$OH: C, 32.88; H, 3.47; N, 5.68. Found: C, 33.32; H, 3.21; N, 5.80.

2-Chloro-4,5-dibromo-1-(2,3,5-tri-O-acetyl-β-D-ribofuranosyl)benzimidazole (84)

To a stirred mixture of 1.228 g (5.498 mmol) of CuBr$_2$ and 0.654 mL (4.949 mmol) of 90% t-BuONO in 10 mL of CH$_3$CN, was added dropwise a solution of 1.170 g (2.748 mmol) of 5-amino-2-chloro-1-(2,3,5-tri-O-acetyl-β-D-ribofuranosyl)benzimidazole in 3 mL of CH$_3$CN. After the addition, stirring was continued at room temperature for 2 h. The reaction mixture was diluted with 100 mL of EtOAc. The EtOAc solution was washed with H$_2$O (100 mL), sat. NaHCO$_3$ solution (100 mL×2), sat. NaCl solution (100 mL), dried (Na$_2$-

SO$_4$), and evaporated. The residue was chromatographed on a silica column (4.1×30 cm, eluted with CHCl$_3$). Evaporation of fractions 59-78 (20 mL per fraction) and recrystallization from MeOH gave 0.600 g (38%) of 84 as a white solid. MP 202°-203° C. MS (EI) m/e 565.9109 (4%, M+ =565.9091). $^1$H NMR (DMSO-d$_6$): δ7.74 (2×d, 2, 6-H and 7-H, J$_{6-7}$=8.5 Hz), 6.26 (d, 1, 1'-H, J$_{1'-2'}$=6.5 Hz), 5.53 (t, 1, 2'-H, J$_{2'-3'}$=7.0 Hz), 5.42 (dd, 1, 3'-H, J$_{3'-4'}$=4.5 Hz), 4.42.

2-Chloro-4,5-dibromo-1-β-D-ribofuranosylbenzimidazole (85)

A solution of 0.529 g (0.930 mmol) of 84 in 25 mL of NH$_3$/MeOH was stirred in a pressure bottle at room temperature for 5 h. Volatile materials were removed by evaporation and coevaporation with MeOH (3 x, bath temperature<40° C.). The resulting solid was recrystallized from MeOH/H$_2$O to give 0.316 g (2 crops, 77%) of 85 as white crystals. MP: 167°-169° C. MS: (CI) m/e 440.8837 (20%, MH+ =440.8852). $^1$H NMR (DMSO-d$_6$): δ8.05 (d, 1, 7-H, J$_{7-6}$=8.5 Hz), 7.59 (d, 1, 6-H), 5.89 (d, 1, 1'-H, J$_{1'-2'}$=7.5 Hz), 5.51 (d, 1, 2'-OH, J$_{2'-2'OH}$=6.5 Hz), 5.28 (d, 1, 3'-OH, J$_{3'-3'OH}$=4.5 Hz), 5.27 (t, 1, 5'-OH, J$_{5'-5'OH}$=5.0 Hz), 4.40 (m, 1, 2'-H, J$_{2'-3'}$=5.5 Hz), 4.13 (m, 1, 3'-H, J$_{3'-4'}$=2.0 Hz), 4.00 (m, 1, 4'-H, J$_{4'-5'}$=J$_{4'-5'}$=3.5 Hz), 3.68 (m, 2, 5'-H and 5''-H, J$_{5'-5''}$=12.0 Hz). $^{13}$H NMR (DMSO-d$_6$): δ141.70 (C2), 141.58 (C3a), 132.21 (C7a), 127.42 (C6), 118.06 (C5), 114.08 (C4), 113.87 (C7), 89.45 (C1'), 86.34 (C4'), 71.74 (C2'), 69.62 (C3'), 61.07 (C5'). Anal. Calcd. for C$_{12}$H$_{11}$Br$_2$ClN$_2$O$_4$; C, 32.57; H, 2.51; N, 6.33. Found: C, 32.70; H, 2.33; N, 6.33.

2-Chloro-5,6-diiodobenzimidazole

Compound 6-amino-2-chloro-5-iodobenzimidazole (0.190 g, 0.647 mmol) was dissolved in a mixture of Conc. H$_2$SO$_4$/ice-H$_2$O (2 mL/3 mL) at 0° C. To this mixture, was added dropwise a solution of NaNO$_2$/H$_2$O (0.134 g, 1.942 mmol/5 mL). The reaction mixture was stirred at room temperature for 1 h. A solution of KI/H$_2$O (0.537 g/5 mL) was added dropwise and stirring was continued at room temperature for 3 h and then 100° C. for 15 min. The reaction mixture was extracted with EtOAc (50 mL×2). The EtOAc solution was washed with Na$_2$S$_2$O$_3$/H$_2$O (1 g/50 mL), sat. NaHCO$_3$ (50 mL), sat. NaCl solution (50 mL), dried (Na$_2$SO$_4$), and evaporated. The residue was recrystallized from MeOH to give 0.169 g of a yellowish crystalline compound. The mother liquor was evaporated and the residue was chromatographed on a silica column (2×4 cm, eluted successively with 1%, 2% MeOH/CHCl$_3$). Evaporation of fractions 4-6 (20 mL per fraction) and recrystallization from MeOH gave an additional 0.040 g of product. The total yield was 0.209 g (80%). MP: 228°-229° C. (dec). MS: (EI) m/e 403.8064 (100%, M+ =403.8074). $^1$H NMR (DMSO-d$_6$): δ13.50 (br s, 1, 1-NH), 8.11 (s, 2, 4-H and 7-H). Anal. Calcd. for C$_7$H$_3$ClI$_2$N$_2$: C, 20.79; H, 0.75; N, 6.93. Found: C, 20.73; H, 0.83; N, 6.74.

2-Chloro-5,6-diiodo-1-β-D-ribofuranosylbenzimidazole (107)

To a suspension of 0.230 g (0.569 mmol) of 2-chloro-5,6-diiodobenzimidazole in 5 mL of MeCN, was added 0.140 mL (0.569 mmol) of BSA. The reaction mixture was stirred at 80° C. for 15 min to give a clear solution. This solution was treated with 0.199 g (0.626 mmol) of 1,2,3,5-tetra-O-acetyl-β-D-ribofuranose and 0.132 mL (0.683 mmol) of TMSOTf at 80° C. for 45 min. The reaction mixture was cooled and diluted with EtOAc (50 mL). The EtOAc solution was washed with sat. NaHCO$_3$ solution (50 mL×2), sat. NaCl solution (50 mL), dried (Na$_2$SO$_4$), and evaporated The residue was chromatographed on a silica column (2.4×15 cm, eluted with CHCl$_3$). Evaporation of fractions 18-25 (20 mL per fraction) and recrystallization from MeOH gave 0.157 g (42%) of the blocked nucleoside as white crystals. MP: 120°-123° C. MS: (EI) m/e 661.8823 (14%, M+ =661.8814). $^1$H NMR (DMSO-d$_6$): δ8.34 (s, 1, 7-H), 8.25 (s, 1, 4-H), 6.22 (d, 1, 1'-H, J$_{1'-2'}$=7.0 Hz), 5.54 (t, 1, 2'-H, J$_{2'-3'}$=7.0 Hz), 5.41 (dd, 1, 3'-H, J$_{3'-4'}$=4.5 Hz), 4.46, 4.36 (2×m, 3, 4'-H and 5'—H), 2.16, 2.14, 2.01 (3×s, 9, 3×Ac). $^{13}$H NMR (DMSO-d$_6$): δ169.94, 169.45, 169.15 (3×COCH$_3$), 142.54 (C3a), 140.67 (C2), 134.08 (C7a), 128.88 (C4), 121.48 (C7), 101.98, 101.32 (C5 and C6), 86.53 (C1'), 79.48 (C4'), 70.51 (C2'), 68.71 (C3'), 62.57 (C5'), 20.90, 20.27, 19.98 (3×COCH$_3$). Anal. Calcd. for C$_{18}$H$_{17}$ClI$_2$N$_2$O$_7$: C, 32.63; H, 2.59; N, 4.23. Found: C, 32.81; H, 2.83; N, 4.25. This compound was deprotected to afford compound 107.

2,5,6-Trichloro-1-(2'-deoxy-3,5-di-O-p-toluoyl-β-D-erythro-pentofuranosyl)benzimidazole (110)

To a suspension of 4.43 g (20 mmol) of 2,5,6-trichlorobenzimidazole in 100 mL of dry MeCN, was add portionwise 1.2 g (30 mmol) of 60% NaH in oil at room temperature. After the addition had been completed, the reaction mixture was stirred at room temperature for 20 min. to give a nearly clear yellowish solution. To this solution, compound 3,5-di-O-p-toluyl-β-D-erythro-pentofuranosyl chloride (9.332 g, 24 mmol) was added portionwise over 20 min and stirring was continued at room temperature for an additional 2 h. The reaction mixture was filtered and the solid was washed with portions of EtOAc (~300 mL). The filtrate was evaporated and the residue was dissolved in the EtOAc washings. This EtOAc solution was washed with half sat. NaCl solution (150 mL×2), dried (Na$_2$SO$_4$), and evaporated. The residue was added to 100 mL of MeOH, the mixture was heated at reflux temperature for 5 min. was then allowed to cool to room temperature. Filtration of the resulting suspension and washing the solid with portions of MeOH gave 10.21 g (89%, 2 crops) of 110 as white crystals. MP: 168°-169° C. MS: (EI) m/e 572.0664 (0.5%, M+ =572.0673). $^1$H NMR (DMSO-d$_6$): δ8.04, 7.94 (2×s, 2, 7-H and 4-H), 7.97, 7.86, 7.37, 7.29 (4×d, 8, Ph, J=8.0 Hz), 6.56 (dd, 1, 1'-H, J$_{1'-2'}$=8.5 Hz, J$_{1'-2''}$=6.0 Hz), 5.75 (m, 1, 3'-H, J$_{3'-2'}$=8.0 Hz, J$_{3'-2''}$=2.0 Hz, J$_{3'-4'}$=3.5 Hz), 4.72 (dd, 1, 5'-H, J$_{5'-4'}$=3.5 Hz, J$_{5'-5''}$=12.0 Hz), 4.69 (dd, 1, 5''-H, J$_{5''-4'}$=5.0 Hz), 4.61 (m, 1, 4'-H), 3.02 (m, 1, 2'-H, J$_{2'-2''}$=14.5Hz), 2.72 (m, 1, 2''-H), 2.40, 2.36 (2×s, 6, 2×Me). $^{13}$C NMR (DMSO-d$_6$): δ165.48, 165.34 (2×p-MePhCO), 144.05, 143.81 (2×p-MePhCO), 141.38 (C2), 140.81 (C3a), 132.43 (C7a), 129.48, 129.24 (2×p-MePhCO), 126.47, 126.39, 126.23, 125.91 (2×p-MePhCO, C6, and C5), 120.29 (C4), 113.43 (C7), 85.19 (C1'), 80.07 (C4'), 73.52 (C3'), 63.72 (C5'), 35.75 (C2'), 21.14, 21.09 (2×p-MePhCO). Anal. Calcd. for C$_{28}$H$_{23}$Cl$_3$N$_2$O$_5$: C, 58.60; H, 4.04; N, 4.88. Found: C, 58.35; H, 4.09; N, 4.83.

1-(2'-Deoxy-β-D-erythro-pentofuranosyl) 2,5,6-trichlorobenzimidazole(111)

A suspension of 7.30 g (12.721 mmol) of 110 and 8.284 g (127.21 mmol) of KCN in 255 mL of 90% aq. EtOH was stirred at room temperature for 4 days. The reaction mixture was filtered and the filtrate was evaporated. The resulting solid was triturated successively with $H_2O$ (50 mL×3), hexane (50 mL×3), $CHCl_3$ (50 mL), and was then recrystallized from MeOH to give 3.027 g (70%, 2 crops) of 111 as white crystals. MP: 178°–180° C. MS: (EI) m/e 335.9831 (12%, M+ = 335.9835). $^1H$ NMR (DMSO-$d_6$): δ8.44 (s, 1, 7-H), 7.94 (s, 1, 4-H), 6.35 (dd, 1, 1'-H, $J_{1'-2'}$=9.0 Hz, $J_{1'-2''}$=6.0 Hz), 5.42 (d, 1, 3'-OH, $J_{3'-3'OH}$=4.5 Hz), 5.24 (t, 1, 5'—OH, $J_{5'-5'OH}$=5.0 Hz), 4.43 (m, 1, 3'-H, $J_{3'-2'}$=7.0 Hz, $J_{3'-2''}$=2.0 Hz, $J_{3'-4'}$=2.5 Hz), 3.90 (m, 1, 4'-H, $J_{4'-5'}$=3.0 Hz), 3.70 (dd, 2, 5'-H), 2.51 (m, 1, 2'-H, $J_{2'-2''}$=13.5 Hz), 2.19 (m, 1, 2''—H). $^{13}C$ NMR (DMSO-$d_6$): δ141.21 (C2), 140.95 (C3a), 132.27 (C7a), 125.91, 125.67 (C5 and C6), 120.02 (C4), 114.77 (C7), 87.68 (C4'), 85.70 (C1'), 69.99 (C3'), 60.86 (C5'), 38.96 (C2'). Anal. Calcd. for $C_{12}H_{11}Cl_3N_2O_3$: C, 42.69; H, 3.28; N, 8.30. Found: C, 42.40; H, 3.36; N, 8.07.

1-(2'-Deoxy-β-D-erythro-pentofuranosyl)2-bromo-5,6-dichlorobenzimidazole (112)

To a suspension of 1.55 g (5.829 mmol) of 2-bromo-5,6-dichlorobenzimidazole in 30 mL of dry MeCN, was add portionwise 0.35 g (8.750 mmol) of 60% NaH in oil at room temperature. After the addition had been completed, the reaction mixture was stirred at room temperature for 20 min. to give a nearly clear yellowish solution. To this solution, the appropriate carbohydrate (2.72 g, 6.995 mmol) was added portionwise over 20 min and stirring was continued at room temperature for an additional 2.5 h. The reaction mixture was diluted with EtOAc (100 mL), filtered and the solid was washed with portions of EtOAc (20 mL). This EtOAc solution was washed with half sat. NaCl solution (100 mL×2), dried ($Na_2SO_4$), and evaporated. The residue was chromatographed on a silica column (4×16 cm, eluted with pure chloroform). Evaporation of fractions 18–91 and recrystallization of the residue from EtOH gave 2.927 g (81%, 2 crops) of the protected nucleoside as white crystals. MP: 157°–159° C. MS: (EI) m/e 616.0153 (0.2%, M+ = 616.0167). $^1H$ NMR (DMSO-$d_6$): δ8.02, 7.95 (2×s, 2, 7-H and 4-H), 7.96, 7.86, 7.37, 7.29 (4×d, 8, Ph, J=8.0 Hz), 6.52 (dd, 1, 1'-H, $J_{1'-2'}$=9.0 Hz, $J_{1'-2''}$=6.0 Hz), 5.76 (m, 1, 3'-H, $J_{3'-2'}$=8.0 Hz, $J_{3'-2''}$=2.0 Hz, $J_{3'-4'}$=3.5 Hz), 4.71 (m, 2, 5'-H and 5''-H, $J_{5'-4'}$=4.0 Hz, $J_{5''-4'}$=4.5 Hz, $J_{5'-5''}$=12.0 Hz), 4.63 (m, 1, 4'-H), 3.00 (m, 1, 2'-H, $J_{2'-2''}$=14.5 Hz), 2.70 (m, 1, 2''-H), 2.40, 2.36 (2×s, 6, 2×Me). $^{13}C$ NMR (DMSO-$d_6$): δ165.45, 165.27 (2×p-MePhCO), 144.00, 143.75 (2×p-MePhCO), 142.44 (C3a), 132.49 (C7a), 131.46 (C2), 129.40, 129.19 (2×p-MePhCO), 126.43, 126.36, 126.03, 125.77 (2×p-MePhCO, C6, and C5), 120.12 (C4), 113.29 (C7), 86.27 (C1'), 80.97 (C4'), 73.50 (C3'), 63.71 (C5'), 35.81 (C2'), 21.08, 21.03 (2×p-MePhCO). Anal. Calcd. for $C_{28}H_{23}BrCl_2N_2O_5$: C, 54.39; H, 3.75; N, 4.53. Found: C, 54.54; H, 3.59; N, 4.44.

A suspension of 0.618 g (1.0 mmol) of the protected nucleoside and 0.330 g (5.0 mmol) of KCN in 20 mL of 90% aq. EtOH was stirred at room temperature for 5 days. The reaction mixture was evaporated. The resulting solid was triturated successively with $H_2O$ (10 mL×3), $CHCl_3$ (10 mL×3), and was then recrystallized from EtOH to give 0.300 g (79%, 3 crops) of 112 as white crystals. MP: 187°–188° C. MS: (EI) m/e 379.9332 (6%, M+ = 379.9330). $^1H$ NMR (DMSO-$d_6$): δ8.48 (s, 1, 7-H), 7.93 (s, 1, 4-H), 6.33 (dd, 1, 1'-H, $J_{1'-2'}$=9.0 Hz, $J_{1'-2''}$=5.5 Hz), 5.48 (d, 1, 3'-OH, $J_{3'-3'OH}$=4.0 Hz), 5.31 (t, 1, 5'-OH, $J_{5'-5'OH}$=4.5 Hz), 4.43 (m, 1, 3'-H, $J_{3'-2'}$=6.5 Hz, $J_{3'-2''}$=1.5 Hz), 3.91 (m, 1, 4'—H), 3.71 (m, 2, 5'-H), 2.50 (m, 1, 2'-H, $J_{2'-2''}$=13.5 Hz), 2.15 (m, 1, 2''-H). $^{13}C$ NMR (DMSO-$d_6$): δ142.56 (C3a), 132.49 (C7a), 131.39 (C2), 125.75, 125.56 (C5 and C6), 119.83 (C4), 114.66 (C7), 87.68 (C4'), 86.94 (C1'), 70.02 (C3'), 60.86 (C5'), 39.00 (C2'). Anal. Calcd. for $C_{12}H_{11}BrCl_2N_2O_3$: C, 37.73; H, 2.90; N, 7.33. Found: C, 38.18; H, 2.80; N, 7.30.

5-Bromo-2,6-dichloro-1-β-D-ribofuranosylbenzimidazole (95)

To a suspension of 0.319 g (1.0 mmol) of 2,6-dichloro-1-β-D-ribofuranosylbenzimidazole in 10 mL of $H_2O$, was added dropwise a sat. solution of $Br_2/H_2O$ at room temperature. After the addition has been completed, stirring was continued for 3 h. The reaction mixture was filtered and the solid was washed with portions of $H_2O$, and then recrystallized from MeOH to give 0.335 g (78%, as M MeOH) of 95 as white crystalline needles. MP 140°–142° C. MS (EI) m/e 395.9274 (2%, M+ = 395.9279). $^1H$ NMR (DMSO-$d_6$): δ8.88 (s, 1, 7-H), 8.08 (s, 1, 4-H), 5.89 (d, 1, 1'-H, $J_{1'-2'}$=8.0 Hz), 5.49 (d, 1, 2'-OH, $J_{2'-2'OH}$=6.5 Hz), 5.40 (t, 5'-OH, $J_{5'-5'OH}$=4.0 Hz), 5.28 (d, 1, 3'-OH, $J_{3'-3'OH}$=4.5 HZ), 4.42 (m, 1, 2'-H, $J_{2'-3'}$=5.5 Hz), 4.13 (m, 1, 3'-H, $J_{3'-4'}$=1.5 Hz), 4.01 (m, 1, 4'-H, $J_{4'-5'}$=$J_{4'-5''}$=2.5 Hz), 3.70 (m, 2, 5'-H and 5''-H, $J_{5'-5''}$=12.0 Hz). Anal. Calcd. for $C_{12}H_{11}BrCl_2N_2O_4$ MeOH: C, 36.30; H, 3.51; N, 6.51. Found: C, 35.98; H, 3.60; N, 6.39.

6-Bromo-2,5-dichloro-1-β-D-ribofuranosylbenzimidazole (99)

To a suspension of 0.110 g (0.313 mmol, as $C_{12}H_{12}Cl_2N_2O_4$ MeOH) of 2,5-dichloro-1-β-D-ribofuranosylbenzimidazole in 3 mL of $H_2O$ was added dropwise 10 mL of a sat. solution of $Br_2/H_2O$ at room temperature. After the addition has been completed, stirring was continued for 6 h. The reaction mixture was filtered and the solid was washed with portions of $H_2O$, and then recrystallized from MeOH to give 0.091 g (73%, 2 crops) of 99 as white crystalline needles. MP 158°–159° C. MS (EI) m/e 395.9274 (5% M+ = 395.9279). $^1H$ NMR (DMSO-$d_6$): δ8.69 (s, 1, 7-H), 7.96 (s, 1, 4-H), 5.88 (d, 1, 1'-H, $J_{1'-2'}$=8.0 Hz), 5.51 (d, 1, 2'-OH, $J_{2'-2'OH}$=6.5 Hz), 5.41 (t, 5'-OH, $J_{5'-5'OH}$=4.5 Hz), 5.30 (d, 1, 3'-OH, $J_{3'-3'OH}$=4.5 Hz), 4.42 (m, 1, 2'-H, $J_{2'-3'}$=5.5 Hz), 5.30 (d, 1, 3'-OH, $J_{3'-4'}$=1.5 Hz), 4.01 (m, 1, 4'-H, $J_{4'-5'}$=$J4'-5'$=2.5 Hz), 371 (m, 2, 5'-H and 5''-H, $J_{5'-5''}$=1.20 Hz). Anal. Calcd. for $C_{12}H_{11}BrCl_2N_2O_4$: C, 36.21; H, 2.79; N, 7.04. Found: C, 36.14; H, 2.90; N, 6.90.

D. Testing of Compounds

The following test methods were followed in generating the data in FIGS. 3 through 8.

1. In Vitro Testing in Cell Culture a. Methods (1) Propagation of Cells and Viruses (a) Cells The routine growth and passage of KB cells—a human epidermoid neoplastic cell line—was performed in monolayer cultures using minimal essential medium (MEM) with either Hanks salts [MEM(H)] or Earle salts ([MEM(E)] supplemented with 10% calf serum or 5 to 10% fetal bovine serum. The sodium bicarbonate concentration was varied to meet the buffering capacity required. BSC-1 (African green monkey kidney) cells were grown and passaged in Dulbecco modified MEM(E) supplemented with 5% tryptose phosphate broth and 5% horse serum. Cultures of human foreskin fibroblasts (HFF) were grown in medium consisting of MEM(E) with 10% fetal bovine serum.

Cells were passaged at 1:2 to 1:10 dilutions according to conventional procedures by using 0.05% trypsin plus 0.02% EDTA in a HEPES buffered salt solution. HFF cells were passaged only at 1:2 dilutions.

(b) Viruses

The S-148 strain of HSV-1 was used in most experiments and was provided by Dr. T. W. Schafer of Schering Corporation. The HF strain of HSV-1 was used in selected experiments and was obtained from Dr. G. H. Cohen, University of Pennsylvania. The Towne strain, plaque-purified isolate $P_o$, of HCMV was a gift of Dr. Mark Stinski, University of Iowa.

High titer HSV-1 stocks have been prepared as follows:

Nearly confluent monolayer cultures of KB cells were grown in 32 oz. glass bottles containing MEM(E) buffered with 25 mM HEPES and supplemented with 5% fetal bovine serum and 0.127 gm/liter L-arginine (VGM, virus growth medium). The cultures were infected at a low input multiplicity to reduce the formation of defective virus. After cell cytopathology reached "three to four plus", the cells were harvested by vigorous shaking, and concentrated by centrifugation (800× g for 5 min.). The resulting virus pools were stored at −76° C. until retrieved for use in experiments.

Stock HCMV was prepared by infecting HFF cells at a multiplicity of infection (m.o.i.) of less that 0.01 plaque-forming units (p.f.u.) per cell. Cell growth medium was changed every four days until cytopathology was evident in all cells (approximately 21 days). Supernatant fluids were retained as the virus stock. Four days later, the remaining cells were disrupted by three cycles of freeze-thawing and the cell plus medium held as an additional source of virus. Storage was in liquid nitrogen.

HSV-1 was titered using monolayer cultures of BSC-1 cells. Cells were planted at $3\times 10^5$ cells/well using 6-well cluster dishes. MEM(E) supplemented with 10% fetal bovine serum was employed as medium. After 22-24 hours, cells were 90% confluent and were inoculated in triplicate using at least three ten-fold dilutions with 0.2 ml of the virus suspension to be assayed and incubated in a humidified 4% $CO_2$-90% air atmosphere for one hour to permit viral adsorption. Following virus adsorption, the cell sheet was overlayed with 5 ml of MEM(E) with 5% serum plus 0.5% methocel (4000 CPS) and incubated an additional two to three days. Cells were fixed and stained with 0.1% crystal violet in 20% methanol and macroscopic plaques enumerated.

HCMV was titered in 24-well cluster dishes which were planted to contain $5\times 10^4$ HFF cells/well, grown as described above. When the cells were 70 to 80% confluent, 0.2 ml of the virus suspension was added per well and adsorbed as described above. At least three ten-fold dilutions of each preparation were used. Following virus adsorption, the cell sheets were overlayed with 0.5% methocel (4000 CPS) in maintenance medium [MEM(E) with 1.1 gm/liter $NaHCO_3$, 100 units/ml penicillin G, 100 μg/ml streptomycin, and 5% fetal bovine serum]. The cultures were incubated in a humidified atmosphere of 4% $CO_2$-96% air. Viral foci were visible 5 to 7 days after infection using at least 10-fold magnification. Cells were fixed and stained by a 10-minute exposure to a 0.1% solution of crystal violet in 20% methanol 7 to 12 days after infection. Microscopic foci were enumerated at 20-fold magnification using a Nikon Profile Projector.

(2) Assays for Antiviral Activity (a) HSV-1

Plaque reduction experiments with HSV-1 were performed using monolayer cultures of BSC-1 cells. The assay was performed exactly as described above except that the 0.2 ml virus suspension contained approximately 100 p.f.u. of HSV-1. Compounds to be tested were dissolved in the overlay medium at concentrations usually ranging from 0.1 to 100 μM in half-or-one $\text{logarithm}_{10}$ dilutions. Titer reduction assays were performed by planting KB cells in 25 cm$^2$ plastic tissue culture flasks 10 to 24 hours prior to infection. At the onset of experiments, logarithmically growing replicate monolayer cultures were 60 to 80% confluent and contained 2.5 to $4.5\times 10^6$ cells/flask. Medium was decanted and the cultures were infected with 2 to 10 p.f.u. of HSV-1 per cell. Virus was contained in 1.0 ml of VGM supplemented with 5% fetal bovine serum. After a 1 hour adsorption period at 37° C., the cell sheet was rinsed twice with 2 ml of VGM without serum to remove unadsorbed virus and 5 ml of VGM containing drugs at three to five selected concentrations added in duplicate. Following an 18- to 20- hour incubation at 37° C., infected monolayers were treated with EDTA-trypsin to suspend the cells; aliquots were removed, subjected to three cycles of freezing and thawing, and stored at −76° C. for subsequent virus assay. Virus was titered on BSC-1 cells as described above.

ELISA techniques according to standard procedures were also used to determine activity against HSV-1.

Drug effects were calculated as a percentage of the reduction in virus titers in the presence of each drug concentration compared to the titer obtained in the absence of drug. Acylovir was used as a positive control in all experiments.

(b) HCMV

The effect of compounds of the replication of HCMV has been measured using both a plaque (focus) reduction assay and a titer (yield) reduction assay. For the former, HFF cells in 24-well culture dishes were infected with approximately 50 p.f.u. of HCMV per well using the procedures detailed above. Compounds dissolved in growth medium were added in three to six selected concentrations to triplicate wells following virus adsorption. Following incubation at 37° C. for 7 to 10 days, cell sheets were fixed, stained and microscopic plaques were enumerated as described above. Drug effects were calculated as a percentage of reduction in number of foci in the presence of each drug concentration compared to the number observed in the absence of drug. DHPG (ganciclovir) was used as a positive control in all experiments.

For titer reduction assays, HFF cells were planted as described above in 24-well cluster dishes or in 25 cm$^2$ flasks. When monolayers were approximately 70% confluent, HCMV was added at a m.o.i. of 0.5 p.f.u. per cell and adsorbed as detailed above. Compounds dissolved in growth medium were added in one or one-half-logarithm$_{10}$ dilutions and incubation continued at 37° C. After 7 to 10 days of incubation, culture dishes of flasks were frozen at 76° C. For titer determination, cells were thawed and then subjected to two more cycles of freezing and thawing at 37° C. Serial, one-logarithm$_{10}$ dilutions of the final suspension were prepared and inoculated onto new cultures of HFF cells. Titer determination was as detailed above in part (1) (b).

(3) Cytotoxicity Assays (a) Protocol for Determining Effects of Compounds of DNA, RNA and Protein Synthesis KB or HFF cells were planted using a Costar Transplate-96 (Costar, Cambridge, Mass.) in Costar 96-well cluster dishes at a concentration of 10,000 to 12,000 cells per well. Cells were suspended in 200 μl of medium [MEM(H) plus 0.7 gm/liter NaHCO$_3$ supplemented with 10% calf serum] per well. After incubation of 16 to 24 hours at 37° C. in a humidified atmosphere of 4% CO$_2$ in air, 150 μl of medium was removed per well. One-hundred μl of medium with or without compounds in twice their final concentrations was added to each well using a Titertek Multichannel Pipette. Final concentrations of compounds ranged from 0.1 to 320 μl of medium containing radioactive precursors also was added to each well to give a final concentration to 1 to 3 μCi/ml of labeled precursor. [$^3$H]Thd was diluted with unlabeled dThd to give a final concentration of 3 to 6 μM.

Following addition of drugs and labeled precursors, plates were incubated as described above for an additional 18 to 24 hours. Logarithmic cell growth occurred during this time with continual uptake of labeled precursors. At the end of the incubation period, cells were individually harvested from each well using a Skatron Cell harvester (Skatron, Inc., Sterling, Va.). Cultures for individual wells were harvested onto filter paper and washed free of unincorporated label with nine sequential washes with 5% trichloroacetic acid, nine washes with water, and nine with ethanol using the Skatron unit. Filters were dried, circles from individual cultures were punched from the filter mat and placed into mini-vials. Liquid scintillation solution was added, and radioactivity determined in a Beckman model LS8100 Liquid scintillation spectrometer. All samples were counted for 2.0 minutes each, with three round of counting. Counts per minute were determined following the application of statistical methods to eliminate count rates which fell outside distribution limits defined by Chauvenetys rejection criterion.

All analyses were performed in triplicate. That is, three culture wells were used per time point, radioactive precursor, and drug concentration in all experiments. Results from triplicate assays were converted to percent of control and plotted as log dose-response curves from which 50% inhibitor (I$_{50}$) concentrations were interpolated. Three concentrations of vidarabine were included on all plates as a positive control.

(b) Visual Scoring

Cytotoxicity produced in HFF and BSC-1 cells was estimated by visual scoring of cells not affected by virus infection in the HCMV and HSV-1 plaque reduction assays. Cytopathology was estimated at 35- and 60-fold magnification and scored on a zero to four plus basis. Wells were scored on the day of staining.

(4) Cell Growth Rates

Population doubling times and cell viability were measured in uninfected HFF and/or KB cells. Cells were planted in replicate 6-well plastic tissue culture dishes or in 25 cm$^2$ flasks as described above in part 1. Following an incubation period during which cells attached to the substrate, medium was decanted, the cell sheet rinsed once with HBS, and fresh medium added. The medium consisted of MEM(E) with 1.1 gm NaHCO$_3$/liter and 10% fetal bovine or calf serum plus appropriate log or half-log concentrations of drug. After additional periods of incubation from 1 to 72 hours at 37° C., cells were harvested by means of 0.05% trypsin plus 0.02% EDTA in a HEPES-buffered salt solution. Cells were enumerated using either a Coulter counter or a homocytometer and viability determining using trypsan blue dye exclusion.

(5) Plating Efficiency

A plating efficiency assay was used to confirm and extend results described above. Briefly, KB cells were suspended in growth medium and an aliquot containing 1000 cells was added to a 140×25 mm petri dish. Growth medium (40 ml) containing selected concentrations of test compounds was added and the cultures incubated in a humidified atmosphere of 4% CO$_2$-96% air, 37° C. for 14 days. Medium then was decanted and colonies fixed with methanol and stained with 0.1% crystal violet in 20% methanol. Macroscopic colonies greater than 1 mm in diameter were enumerated. Drug effects were calculated as a percentage of reduction in number of colonies formed in the presence of each drug concentration compared to the number of colonies formed in the absence of drugs. Dose-response curves were generated and I$_{50}$ concentrations for inhibition of plating/colony formation were calculated.

(6) Data Analysis

Dose-response relationships were used to compare drug effects. These were constructed by linearly regressing the percent inhibition of parameters derived in the preceding sections against log drug concentrations. The 50 inhibitory (I$_{50}$) concentrations were calculated from the regression lines using the methods described by Goldstein. See Goldstein, A., *Biostatistics: An Introductory Test*, MacMillan, New York, 1964, pp. 156-161. The three I$_{50}$ concentrations for inhibition of DNA, RNA and protein synthesis were averaged and were reported in the tables. Along with the I$_{50}$ concentrations are compared to I$_{50}$ concentrations for inhibition for HCMV or HSV-1 replication. Compounds for which the ratio of cytotoxicity I$_{50}$ concentrations to antiviral I$_{50}$ concentrations (in vitro therapeutic index) were greater than 10, were considered for further study.

b. Results in Cell Culture (1) Antiviral Activity and Cytotoxicity of Benzimidazole Nucleosides FIG. 3 summarizes test results from antiviral and cytotoxicity evaluation of the benzimidazoles. These halogen-substituted compounds were active against HCMV, with a halogen at R$_5$ being essential for antiviral activity and low cyctotoxicity. For example, compounds 45 and 52 were active against HCMV in the sub- or low micro molar range and did not produce cytotoxicity in uninfected cells at concentrations up to 100 μM. This potent and selective antiviral activity against HCMV is in sharp contrast to the low, apparent activity against this virus of the dichloro compound commonly referred to as DRB which compound was initially described by Tamm (I. Tamm, *Science* 120:847-848, 1954).

The $R_2$ and $R_3$ positions in this compound are substituted by Cl but the $R_5$ position is unsubstituted. Although this compound appears to have weak activity against HCMV and HSV-1 (FIG. 3), this activity was observed only at concentrations which produced cytotoxicity in uninfected cells (FIGS. 3 and 8). Thus in contrast to compounds disclosed herein, the activity of DRB against HCMV is not actual antiviral activity but rather is a manifestation of cytotoxicity.

Compounds other than 45 and 52 showing good activity against HCMV and low cytotoxicity are compounds 85, 95, 99 and compound 111 (the 2'-deoxyribosyl analog of compound 45). Other compounds with activity include compounds 61, 81, 83a, and 107. All compounds except 81, 95, and 99 also had activity against HSV-1.

(2) Detailed Studies with Compound 45

Because of the potent activity of compound 45 against HCMV and its very low cytotoxicity, this compound has been studied more extensively. Data in FIG. 8 provide evidence that compound 45 is highly specific for human cytomegalovirus. The data show the compound is highly active against this virus but is less active against herpes simplex virus type 1 (HSV-1), herpes simplex virus type 2 (HSV-2), varicella-zoster virus (VZV) and murine cytomegalovirus (MCMV).

Because of this unique and potent activity against HCMV, compound 45 was compared to the known anti-HCMV agent ganciclovir as well as to DRB. FIG. 5 shows that compound 45 is at least as effective as ganciclovir in producing multiple 10-fold reductions in virus titer. Thus, at a concentration of 32 μM compound 45 produced a 100,000-fold reduction in the replication of HCMV. The lack of cytotoxicity of compound 45 in this antiviral activity range is shown in FIG. 6. Data in this figure establish that at 32 to 100 μM compound 45 had little or no effect on the growth of uninfected KB cells. FIG. 7 shows that the inhibitory effects produced by a concentration as high as 320 μM could be reversed by simple removal of the drug from uninfected cells. In contrast FIG. 8 shows the effects of the known compound DRB were fully inhibitory to uninfected cells at 100 μM and these effects could not be reversed by removal of the drug from culture, thereby establishing the cytoxicity of this compound.

The lack of cytotoxicity of compound 45 was further established by plating efficiency experiments. In these experiments, which measure both the ability of cells to grow and to attach to a substrate, compound 45 had no effect at 100 μM.

In additional studies which compared compound 45 to the known drug ganciclovir, it was found that clinically isolated virus which had become resistant to the activity of ganciclovir in patients who had relapsed during its use retained susceptibility to the action of compound 45. Thus, virus resistant to ganciclovir was sensitive to the activity of compound 45. The possibility of combining the use of compound 45 with that of ganciclovir also was explored. In combination studies it was found that the two drugs acted together synergistically, that is effects produced by the use of the two compounds together were greater than effects produced by either compound acting alone at higher doses.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. An antiviral composition comprising a pharmaceutically acceptable carrier and a compound selected from the group consisting of compounds having the following formulas and pharmaceutically acceptable salts and formulations thereof:

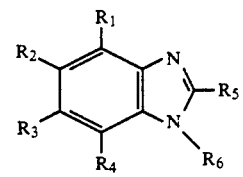

where
$R_1$ is H, $R_2$ and $R_3$ are Cl, $R_4$ is H, $R_5$ is Br and $R_6$ is β-D-ribofuranosyl (compound 52);
$R_1$ is H, $R_2$ and $R_3$ are Cl, $R_4$ is H, $R_5$ is Br and $R_6$ is 2'-deoxy-β-D-ribofuranosyl (compound 112);
$R_1$ is H, $R_2$ and $R_3$ are Cl, $R_4$ is H, $R_5$ is I and $R_6$ is β-D-ribofuranosyl (compound 83a);
$R_1$ is H, $R_2$ and $R_3$ are Cl, $R_4$ is H, $R_5$ is Cl and $R_6$ is 2'-deoxy-β-D-ribofuranosyl (compound 111);
$R_1$ is H, $R_2$ is Br, $R_3$ is Cl, $R_4$ is H, $R_5$ is Cl and $R_6$ is β-D-ribofuranosyl (compound 95);
$R_1$ is H, $R_2$ is Cl, $R_3$ is Br, $R_4$ is H, $R_5$ is Cl and $R_6$ is β-D-ribofuranosyl (compound 99);
$R_1$ is H, $R_2$ and $R_3$ are I, $R_4$ is H, $R_5$ is Cl and $R_6$ is β-D-ribofuranosyl (compound 107);
$R_1$ is H, $R_2$ and $R_3$ are $NO_2$, $R_4$ is H, $R_5$ is Cl and $R_6$ is β-D-ribofuranosyl (compound 61);
$R_1$ and $R_2$ are Br, $R_3$ and $R_4$ are H, $R_5$ is Cl and $R_6$ is β-D-ribofuranosyl (compound 85); and
$R_1$ is Cl, $R_2$ is H, $R_3$ is Cl, $R_4$ is H, $R_5$ is Cl and $R_6$ is β-D-ribofuranosyl (compound 81)

2. A composition of claim 1 wherein:
$R_1$, $R_4$ is H; $R_2$, $R_3$, $R_5$ is Cl and $R_6$ is 2'-deoxy-β-D-ribofuranosyl (compound 111);
$R_1$, $R_4$ is H; $R_2$, $R_3$ is Cl; $R_5$ is Br and $R_6$ is β-D-ribofuranosyl (compound 52); or
$R_3$, $R_4$ is H; $R_1$, $R_2$ is Br; $R_5$ is Cl and $R_6$ is β-D-ribofuranosyl (compound 85).

3. The composition of claim 1 wherein $R_1$, $R_4$ is H; $R_2$, $R_3$ is Cl; $R_5$ is I and $R_6$ is β-D-ribofuranosyl (compound 83a).

4. The composition of claim 1 wherein $R_1$, $R_4$ is H; $R_2$, $R_3$ is $NO_2$; $R_5$ is Cl and $R_6$ is β-D-ribofuranosyl (compound 61).

5. The composition of claim 1 wherein $R_1$, $R_4$ is H; $R_2$, $R_3$ is Cl; $R_5$ is Br and $R_6$ is 2'-deoxy-β-D-ribofuranosyl (compound 112).

6. The composition of claim 1 wherein $R_1$, $R_4$ is H; $R_2$, $R_3$ is I; $R_5$ is Cl and $R_6$ is β-D-ribofuranosyl (compound 107).

7. The composition of claim 1 wherein $R_1$, $R_4$ is H; $R_2$ is Br; $R_3$, $R_5$ is Cl and $R_6$ is β-D-ribofuranosyl (compound 95).

8. The composition of claim 1 wherein is $R_1$, $R_4$ is H; $R_3$ is Br; $R_2$, $R_5$ is Cl and $R_6$ is β-D-ribofuranosyl (compound 99).

9. The composition of claim 1 wherein $R_2$, $R_4$ is H; $R_1$, $R_3$, $R_5$ is Cl and $R_6$ is β-D-ribofuranosyl (compound 81).

10. The composition of claim 2 wherein $R_1$, $R_4$ is H; $R_2$, $R_3$, $R_5$ is Cl and $R_6$ is 2'-D-deoxy-$\beta$-D-ribofuranosyl (compound 111).

11. The composition of claim 2 wherein $R_1$, $R_4$ is H; $R_2$, $R_3$ is Cl; $R_5$ is Br and $R_6$ is $\beta$-D-ribofuranosyl (compound 52).

12. The composition of claim 2 wherein $R_3$, $R_4$ is H; $R_1$, $R_2$ is Br; $R_5$ is Cl and $R_6$ is $\beta$-D-ribofuranosyl (compound 85).

13. An antiviral compound selected from the group consisting of compounds having the following general formulas and pharmaceutically acceptable salts and formulations thereof:

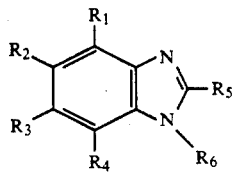

where
$R_1$ is H, $R_2$ and $R_3$ are Cl, $R_4$ is H, $R_5$ is Br and $R_6$ is $\beta$-D-ribofuranosyl (compound 52);

$R_1$ is H, $R_2$ and $R_3$ are Cl, $R_4$ is H, $R_5$ is Br and $R_6$ is 2'-deoxy-$\beta$-D-ribofuranosyl (compound 112);

$R_1$ is H, $R_2$ and $R_3$ are Cl, $R_4$ is H, $R_5$ is I and $R_6$ is $\beta$-D-ribofuranosyl (compound 83a);

$R_1$ is H, $R_2$ and $R_3$ are Cl, $R_4$ is H, $R_5$ is Cl and $R_6$ is 2'-deoxy-$\beta$-D-ribofuranosyl (compound 111);

$R_1$ is H, $R_2$ is Br, $R_3$ is Cl, $R_4$ is H, $R_5$ is Cl and $R_6$ is $\beta$-D-ribofuranosyl (compound 95);

$R_1$ is H, $R_2$ is Cl, $R_3$ is Br, $R_4$ is H, $R_5$ is Cl and $R_6$ is $\beta$-D-ribofuranosyl(compound 99);

$R_1$ is H, $R_2$ and $R_3$ are I, $R_4$ is H, $R_5$ is Cl and $R_6$ is $\beta$-D-ribofuranosyl (compound 107);

$R_1$ is H, $R_2$ and $R_3$ are NO$_2$, $R_4$ is H, $R_5$ is Cl and $R_6$ is $\beta$-D-ribofuranosyl (compound 61); and $R_1$ and $R_2$ are Br, $R_3$ and $R_4$ are H, $R_5$ is Cl and $R_6$ is $\beta$-D-ribofuranosyl (compound 85).

14. A compound of claim 13 wherein:
$R_1$, $R_4$ is H; $R_2$, $R_3$, $R_5$ is Cl and $R_6$ is 2'-deoxy-$\beta$-D-ribofuranosyl (compound 111);

$R_1$, $R_4$ is H; $R_2$, $R_3$ is Cl; $R_5$ is Br and $R_6$ is $\beta$-D-ribofuranosyl (compound 52); or $R_3$, $R_4$ is H; $R_1$, $R_2$ is Br; $R_5$ is Cl and $R_6$ is $\beta$-D-ribofuranosyl (compound 85).

15. The compound of claim 13 wherein $R_1$, $R_4$ is H; $R_2$, $R_3$ is Cl; $R_5$ is I and $R_6$ is $\beta$-D-ribofuranosyl (compound 83a).

16. The composition of claim 13 wherein $R_1$, $R_4$ is H; $R_2$, $R_3$ is NO$_2$; $R_5$ is Cl and $R_6$ is $\beta$-D-ribofuranosyl (compound 61).

17. The compound of claim 13 wherein $R_1$, $R_4$ is H; $R_2$, $R_3$ is Cl; $R_5$ is Br and $R_6$ is 2'-deoxy-$\beta$-D-ribofuranosyl (compound 112).

18. The compound of claim 13 wherein $R_1$, $R_4$ is H; $R_2$, $R_3$ is I; $R_5$ is Cl and $R_6$ is $\beta$-D-ribofuranosyl (compound 107).

19. The compound of claim 13 wherein $R_1$, $R_4$ is H; $R_2$ is Br; $R_3$, $R_5$ is Cl and $R_6$ is $\beta$-D-ribofuranosyl (compound 95).

20. The compound of claim 19 wherein is $R_1$, $R_4$ is H; $R_3$ is Br; $R_2$, $R_5$ is Cl and $R_6$ is $\beta$-D-ribofuranosyl (compound 99).

21. The compound of claim 14 wherein $R_1$, $R_4$ is H; $R_2$, $R_3$, $R_5$ is Cl and $R_6$ is 2'-deoxy-$\beta$-D-ribofuranosyl (compound 111).

22. The compound of claim 14 wherein $R_1$, $R_4$ is H; $R_2$, $R_3$ is Cl; $R_5$ is Br and $R_6$ is $\beta$-D-ribofuranosyl (compound 52).

23. The compound of claim 14 wherein $R_3$, $R_4$ is H; $R_1$, $R_2$ is Br; $R_5$ is Cl and $R_6$ is $\beta$-D-ribofuranosyl (compound 85).

24. An antiviral composition comprising a therapeutically effective amount of a first antiviral agent and a therapeutically effective amount of a second antiviral agent, wherein the first antiviral agent is a compound having the following formula and pharmaceutically acceptable salts and formulations thereof:

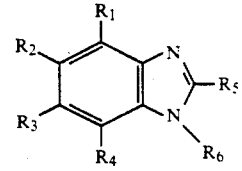

where
$R_1$ is H, $R_2$ and $R_3$ are Cl, $R_4$ is H, $R_5$ is Cl and $R_6$ is $\beta$-D-ribofuranosyl (Compound 45); and the second antiviral agent is ganciclovir.

* * * * *

UNITED STATES PATENT AND TRADEMARK OFFICE
CERTIFICATE OF CORRECTION

PATENT NO. : 5,248,672
DATED : September 28, 1993
INVENTOR(S) : Townsend, et al

Page 1 of 6

It is certified that error appears in the above-indentified patent and that said Letters Patent is hereby corrected as shown below:

On the Title Page Under U.S. Patent Documents, reference 3,311,628, delete "3,311,628  3/1967  Partyka........544/280".

On the Title Page under "Other Publications", second page, Column 2, line 13, "Virto" should be --Vitro--.

Abstract line 3, "particulary" should be --particularly--.

Column 2, line 47, "Cl,." should be --Cl,--.

Column 2, line 60, "are" should be --is--.

Column 4, line 18, after "$R_3$" insert --is--.

Column 5, line 1, ";" should be --.--.

Column 5, line 43, "trichioro" should be --trichloro--.

Column 6, line 15, "method" should be --Method--.

Column 7, lines 62,63, "1-O-acetyl-2,3,5-tri-O-benzoyl-$\beta$-D-ribofuranose" should be --1-O-acetyl-2,3,5-tri-_O_-benzoyl-$\beta$-D-ribofuranose--.

Column 8, line 22, "1,2,3,5-Tetra-O-acetyl-$\beta$-D-ribofuranose" should be --1,2,3,5-Tetra-_O_-acetyl-$\beta$-D-ribofuranose--.

Column 8, lines 25,26, "1,2,3,5-tetra-O-acetyl-D-ribofuranose" should be --1,2,3,5-tetra-_O_-acetyl-D-ribofuranose--.

UNITED STATES PATENT AND TRADEMARK OFFICE
CERTIFICATE OF CORRECTION

PATENT NO. : 5,248,672
DATED : September 28, 1993
INVENTOR(S) : Townsend, et al

It is certified that error appears in the above-indentified patent and that said Letters Patent is hereby corrected as shown below:

Column 8, line 57, "2,3,5-tri-O-benzyl-D-ribofuranosyl" should be --2,3,5-tri-$\underline{O}$-benzyl-D-ribofuranosyl--.

Column 9, lines 30,31, "(m, 1, 4'-H, $J_{4'-5'}=J_{4'-5''}=2.5$ Hz) should be --(m, 1,4'-H, $J_{4'-5'}=J_{4'-5''}=2.5$Hz)--.

Column 9, line 46, "1,2,3,5-tetra-O-acetyl-$\beta$-D-ribofuranose" should be --1,2,3,5-tetra-$\underline{O}$-acetyl-$\beta$-D-ribofuranose--.

Column 9, lines 63,64, "(4%, for $C_{18}H_{17}{}^{35}ClN_2{}^{37}ClN_2O_7$: $M^+=480.0072$)" should be --(4%, for $C_{18}H_{17}{}^{35}Cl_2{}^{37}ClN_2O_7$: $M^+=480.0072$)--.

Column 10, line 1, "(3 x COCH$_3$)" should be --(3 x $\underline{C}$OCH$_3$)--.

Column 10, line 5, "(3 x COCH$_3$)" should be --(3 x CO$\underline{C}$H$_3$)--.

Column 10, lines 36,37, "(2,3,5-tri-O-acetyl-$\beta$-D-ribofuranosyl)" should be --(2,3,5-tri-$\underline{O}$-acetyl-$\beta$-D-ribofuranosyl)--.

Column 10, line 45, "(DMSO-d$_6$)" should be --(DMSO-$\underline{d}_6$)--.

Column 10, line 48, "(DMSO-d$_6$)" should be --(DMSO-$\underline{d}_6$)--.

UNITED STATES PATENT AND TRADEMARK OFFICE
CERTIFICATE OF CORRECTION

PATENT NO. : 5,248,672

DATED : September 28, 1993

INVENTOR(S) : Townsend, et al

It is certified that error appears in the above-indentified patent and that said Letters Patent is hereby corrected as shown below:

Column 10, lines 62,63, "(2,3,5-tri-O-acetyl-β-D-ribofuranosyl)" should be --(2,3,5-tri-$\underline{O}$-acetyl-β-D-ribofuranosyl)--.

Column 11, line 7, "(2xd, 2, 6-H and 7-H, $J_{6,7}$= 8.5 Hz)" should be --(2xd, 2, 6-H and 7-H, $J_{67}$= 8.5 Hz)--.

Column 11, lines 26,27, "(m, 1, 4'-H, $J_{4'.5'}=J_{4'.5'}$=3.5 Hz)" should be --(m, 1, 4'-H, $J_{4'.5'}=J_{4'.5''}$=3.5 Hz)--.

Column 11, line 31, ";" should be --:--.

Column 11, line 58, "$C_7H_3Cll_2N_2$:" should be --$C_7H_3Cl_2N_2$:--.

Column 11, line 68, "1,2,3,5-tetra-O-acetyl-β-D-ribofuranose" should be --1,2,3,5-tetra-$\underline{O}$-acetyl-β-D-ribofuranose--.

Column 12, line 5, after "evaporated" insert --.--.

Column 12, line 17, "(3 x COCH$_3$)" should be --(3 x $\underline{C}$OCH$_3$)--.

Column 12, line 21, "(3 x COCH$_3$)" should be --(3 x CO$\underline{C}$H$_3$)--.

Column 12, line 21, "$C_{18}H_{17}Cll_2N_2O_7$:" should be --$C_{18}H_{17}Cl_2N_2O_7$:--.

UNITED STATES PATENT AND TRADEMARK OFFICE
CERTIFICATE OF CORRECTION

PATENT NO. : 5,248,672
DATED : September 28, 1993
INVENTOR(S) : Townsend, et al

It is certified that error appears in the above-indentified patent and that said Letters Patent is hereby corrected as shown below:

Column 12, line 26, "toluoyl" should be --toluyl--.

Column 12, line 30, "add" should be --added--.

Column 12, lines 35,36, "3,5-di-O-p-toluyl-β-D-erythro-pentofuranosyl" should be --3,5-di-O-p-toluyl-β-D-erythro-pentofuranosyl--.

Column 12, lines 59,60, "(2xp-MePhCO)" should be --(2xp-Me-PhCO)--.

Column 12, line 60, "(2xp-MePhCO)" should be --(2xp-MePhCO)--.

Column 12, lines 61,62, "(2xp-MePhCO)" should be --(2xp-MePhCO)--.

Column 12, lines 62,63, "(2xp-MePhCO)" should be --(2xp-MePhCO)--.

Column 12, line 66, "(2xp-MePhCO)" should be --(2xp-MePhCO)--.

Column 13, line 30, "add" should be --added--.

Column 13, line 55, "(2xp-MePhCO)" should be --(2xp-MePhCO)--.

Column 13, line 56, "(2xp-MePhCO)" should be --(2xp-MePhCO)--.

Column 13, line 57, "(2xp-MePhCO)" should be --(2xp-MePhCO)--.

UNITED STATES PATENT AND TRADEMARK OFFICE
CERTIFICATE OF CORRECTION

PATENT NO. : 5,248,672
DATED : September 28, 1993
INVENTOR(S) : Townsend, et al

Page 5 of 6

It is certified that error appears in the above-indentified patent and that said Letters Patent is hereby corrected as shown below:

Column 13, line 58, "(2xp-MePhCO, C6, and C5)" should be --(2xp-MePhCO, C6, and C5)--.

Column 13, lines 60,61, "(2xp-MePhCO)" should be --(2xp-MePhCO)--.

Column 14, line 31, "HZ" be --Hz--.

Column 14, line 55, "J4'-5'" be --$J_{4',5'}$--.

Column 15, line 5, delete "(".

Column 15, line 40, "that" should be --than--.

Column 17, line 14, "of" should be --on--.

Column 19, line 45, "cytoxicity" should be --cytotoxicity".

Column 20, line 39, Claim 1, after "(compound 81)" insert --.--.

Column 20, line 63, Claim 8, delete "is".

Column 21, line 2, Claim 10, "2'-D-deoxy-$\beta$-D-ribofuranosyl" should be --2'-deoxy-$\beta$-D-ribofuranosyl--.

UNITED STATES PATENT AND TRADEMARK OFFICE
CERTIFICATE OF CORRECTION

PATENT NO. : 5,248,672
DATED : September 28, 1993
INVENTOR(S) : Townsend, et al

It is certified that error appears in the above-indentified patent and that said Letters Patent is hereby corrected as shown below:

Column 22, line 18, Claim 20, "19" should be --13--.

Column 22, line 18, Claim 20, delete "is".

Signed and Sealed this

Sixth Day of September, 1994

Attest:

BRUCE LEHMAN

Attesting Officer

Commissioner of Patents and Trademarks